US008007278B2

(12) United States Patent
Chao

(10) Patent No.: US 8,007,278 B2
(45) Date of Patent: Aug. 30, 2011

(54) PERIODONTAL SURGERY OPERATION METHODS AND INSTRUMENTS

(76) Inventor: John Chao, San Gabriel, CA (US)

(*) Notice: Subject to any disclaimer, the term of this patent is extended or adjusted under 35 U.S.C. 154(b) by 155 days.

(21) Appl. No.: 11/498,619

(22) Filed: Aug. 3, 2006

(65) Prior Publication Data
US 2007/0031788 A1 Feb. 8, 2007

Related U.S. Application Data

(60) Provisional application No. 60/706,247, filed on Aug. 4, 2005.

(51) Int. Cl.
*A61C 3/02* (2006.01)
(52) U.S. Cl. ............................................... 433/144
(58) Field of Classification Search .......... 433/141–145, 433/25; 606/167
See application file for complete search history.

(56) References Cited

U.S. PATENT DOCUMENTS

| 4,743,198 | A | * | 5/1988 | Kennedy | 433/143 |
| 5,004,419 | A | * | 4/1991 | Kline | 433/143 |
| 6,309,219 | B1 | | 10/2001 | Robert | |
| 6,382,974 | B1 | | 5/2002 | Garfinkel | |
| 7,077,653 | B2 | * | 7/2006 | Haab | 433/143 |
| 2002/0102400 | A1 | * | 8/2002 | Gorokhovsky et al. | 428/336 |

FOREIGN PATENT DOCUMENTS
WO WO-03/047452 A0 6/2003

OTHER PUBLICATIONS

Blackwell Synergy—Endodontic Topics—vol. 11 Issue 1 p. 179—Jul. 2005—"Soft Tissue Management: Suturing and Wound Closure"—Peter Velvart Christine I. Peters; Ove A. Peters.
Periodontal Surgery—Module I—Gingival Surgery—Text by the Department of Periodontics—University of Washington—Objectives of Gingival Surgery Unit—pp. 1-25.
PCT International Search Report and Written Opinion report dated Sep. 17, 2007 from corresponding PCT application PCT/US06/30561.

(Continued)

*Primary Examiner* — Cris L Rodriguez
*Assistant Examiner* — Sunil K Singh
(74) *Attorney, Agent, or Firm* — Foley & Lardner LLP

(57) ABSTRACT

The present invention relates generally to methods of performing periodontal surgeries, and instruments for performing said surgeries. A method of performing periodontal surgery to correct a gingival defect of a patient according to a general embodiment comprises the steps of making an incision at or near a fornix of the patient near the gingival defect, inserting an instrument into the incision to detach a flap, advancing the flap horizontally without enlarging the incision, elevating a papilla within the flap, stretching the flap to cover the gingival defect, and pressing against the flap to promote fibrin formation. An instrument for performing periodontal surgery according to one general embodiment comprises a handle, a first shank connecting to and extending from the handle, a connector section, and a blade section. The connector section further comprises a first end and a second end, wherein the first end connects to the first shank at a first angle, and the second end connects to the blade section at a second angle. Further, the blade section is approximately perpendicular to a plane formed by the handle and the connector section, and a cutting surface of the blade section is parallel to the second end of the connector section.

34 Claims, 16 Drawing Sheets

OTHER PUBLICATIONS

Photo(1): Dental Instruments ("Goldman Knife"); Photo (2): Dental Instruments ("Goldman Knife"); Photo (3) Dental Instruments ("Goldman Knife");Photo (4): Angled Dental Instruments; Photo(5): Dental Instruments:Photo (6): Angled Dental Instruments:Photo (7): Angled Dental Instruments:Photo (8): Dental Instruments.

US Office Action dated Dec. 22, 2010 from related patent application No. 061843-0205 12/212/193.

Canadian Examiner's Report dated Apr. 27, 2009 from related Canadian Patent Application No. 2,616,140.

European Search Report dated Jul. 21, 2009 from related European Patent Application No. 06789457.6-2318.

US Office Action dated Jun. 9, 2010 from related U.S. Appl. No. 12/212,193.

* cited by examiner

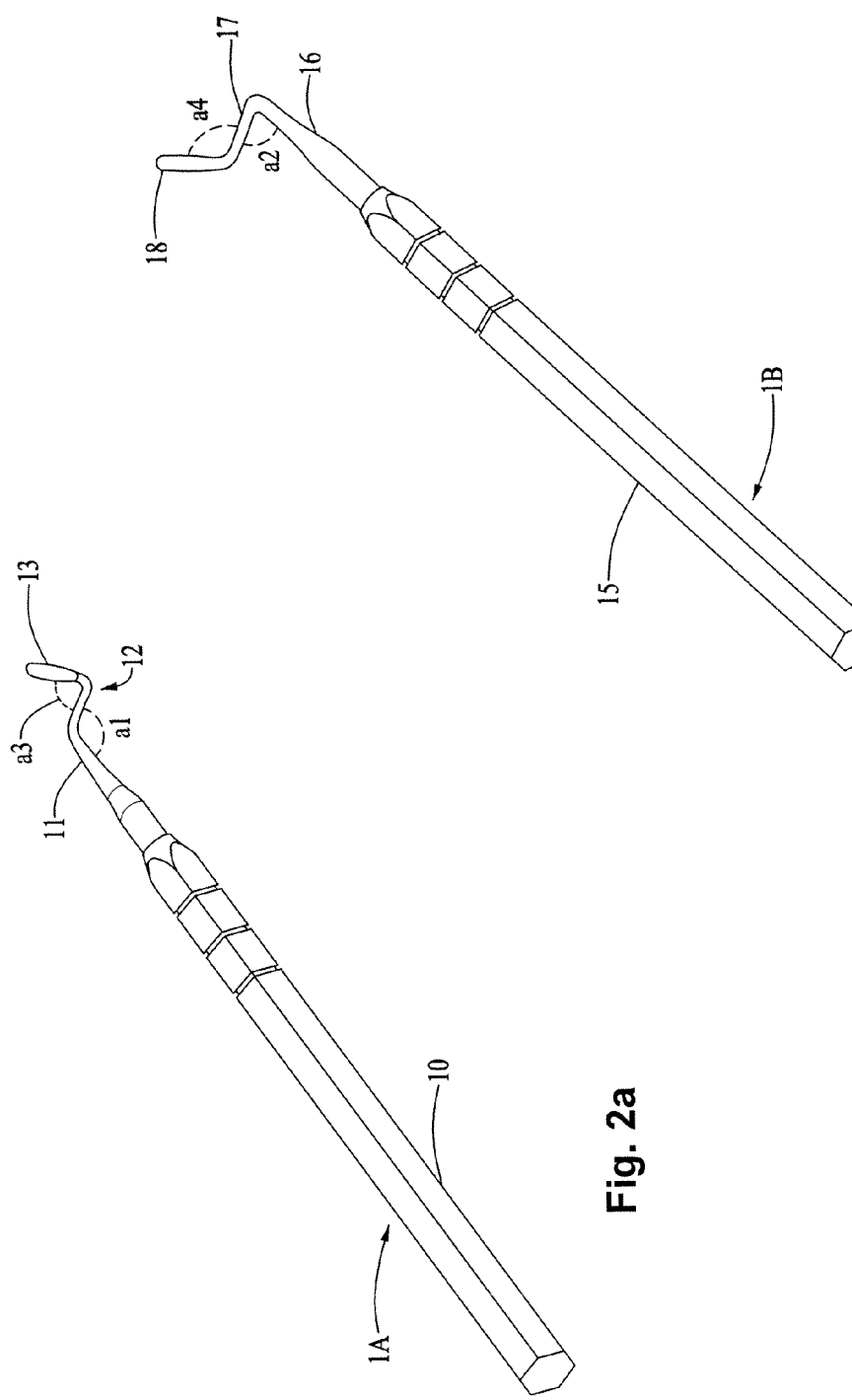

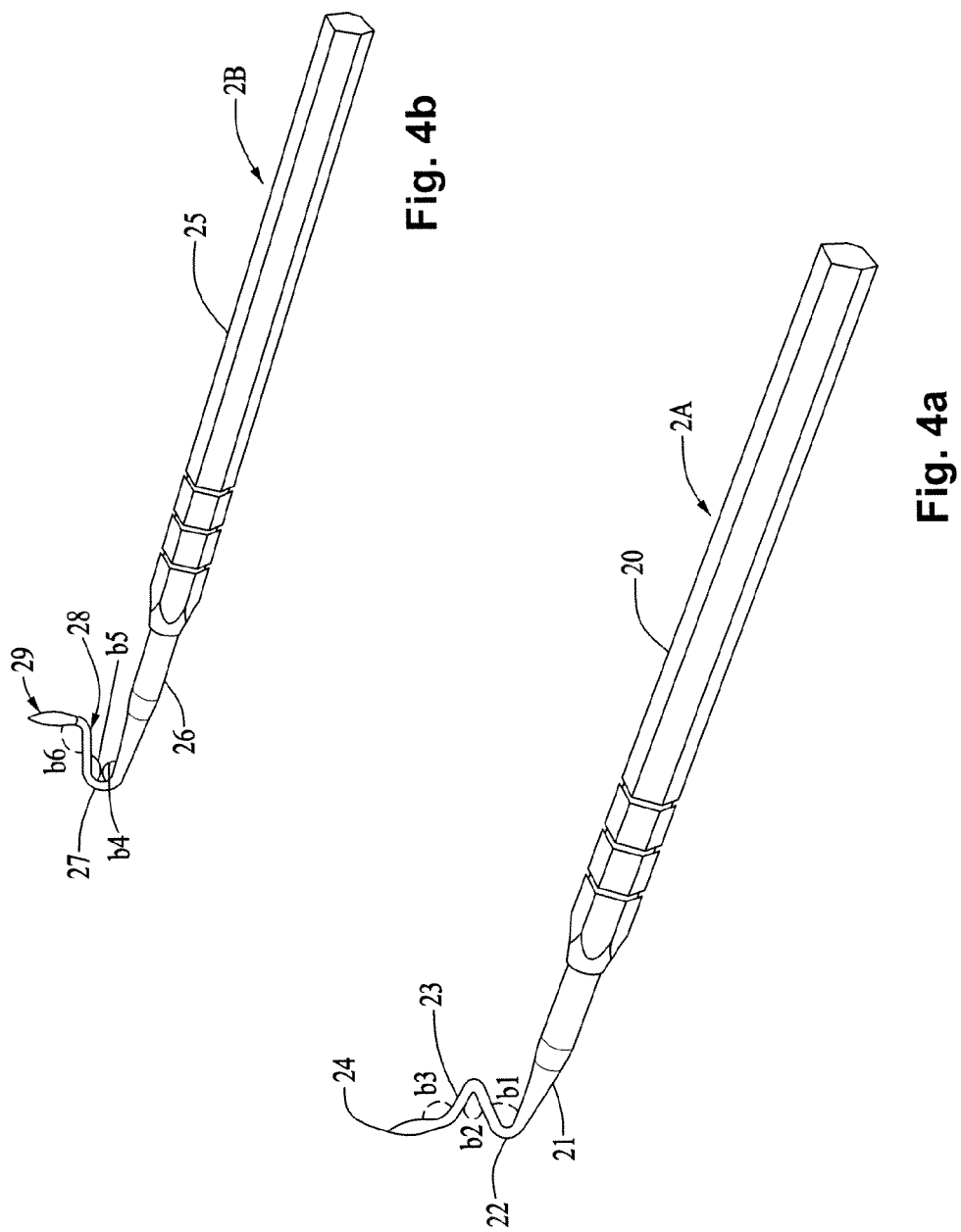

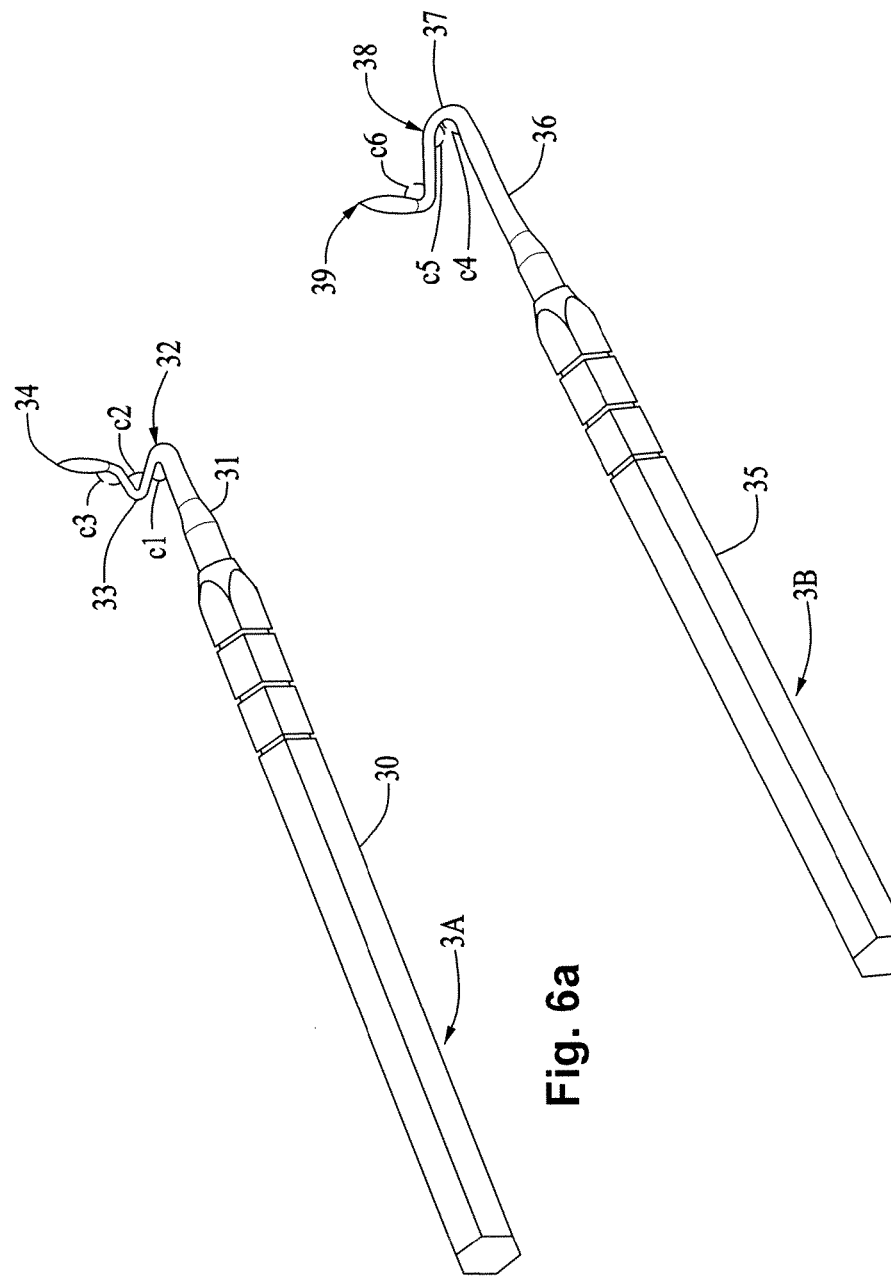

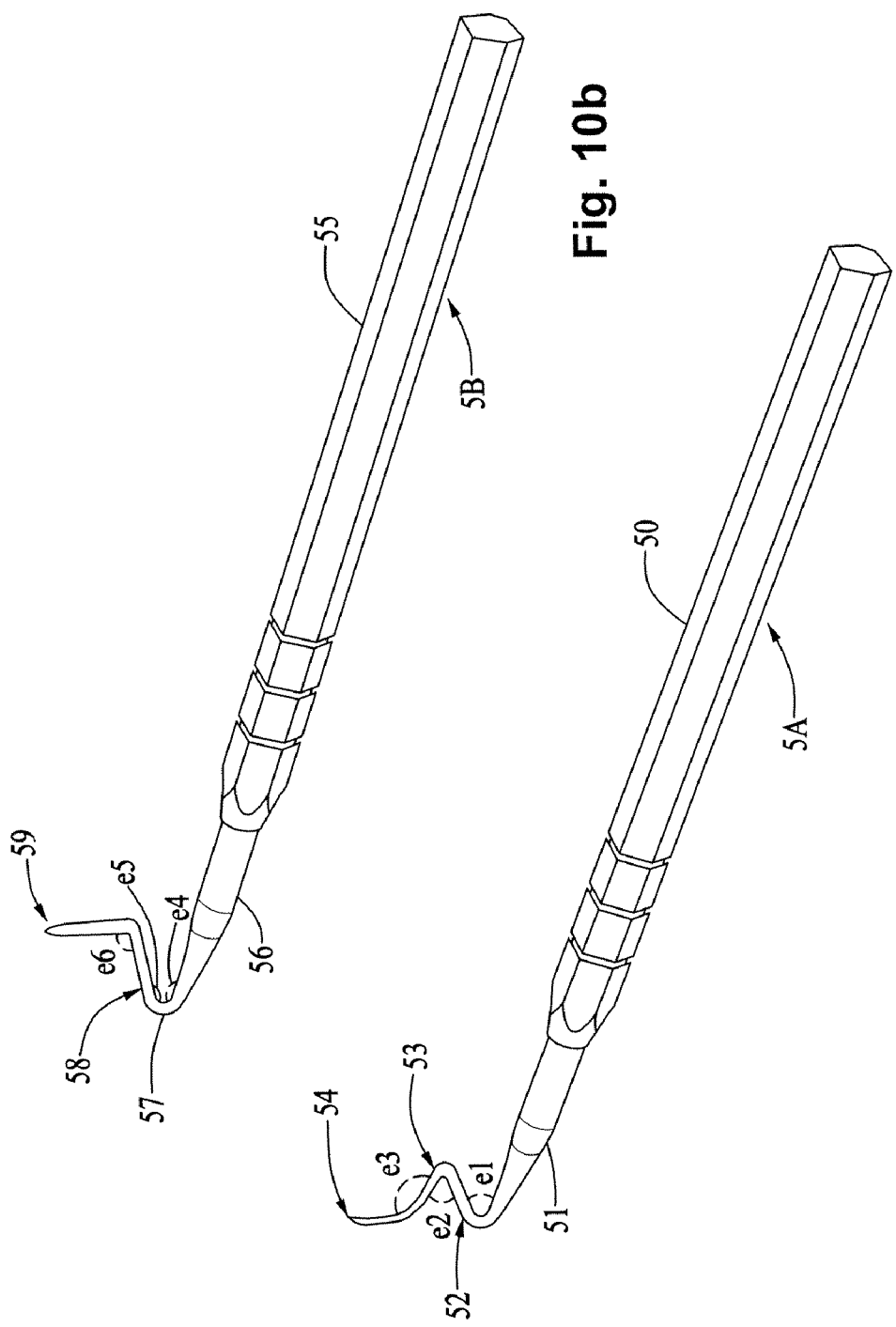

PERIODONTAL SURGERY OPERATION METHODS AND INSTRUMENTS

CROSS-REFERENCE TO RELATED PATENT APPLICATIONS

This application claims priority under 35 USC §119(e) from U.S. Provisional Application Ser. No. 60/706,247, filed Aug. 4, 2005, entitled "Chao Single Invisible Incision Transmucosal Flap with Papillae Elevation and Augmentation Approach," the entirety of which is incorporated herein by reference.

BACKGROUND OF THE INVENTION

1. Field of the Invention

The present invention relates generally to methods of performing periodontal surgeries, and instruments for performing said surgeries.

2. Related Art

Gum diseases, such as periodontitis and gingivitis, can cause damages to the gum near the root of a tooth. In some cases, the gum line near a tooth can recede, exposing the root of the tooth in a condition known gingival recession. The receded gum line is called a gingival defect. The gingival defect of a receding gum near the root of a tooth is unsightly, can cause discomfort, and can lead to severe damages to the gum and tooth.

When a gingival defect becomes severe, it is sometimes necessary to use periodontal surgeries to correct this defect. There are several conventional methods of performing gingival defect correction surgeries (also known as gingival augmentation surgeries).

A common approach (for root coverage) involves making large incisions and grafting tissues to the gum to cover the gingival defect. First, a horizontal incision is made along the gum line where the gum comes into contact with the teeth (also known as the gingival margin). This horizontal incision is made around the effected tooth or group of teeth and the immediately adjacent teeth. Next, two vertical incisions, along the length direction of the teeth, are made at the two ends of the horizontal incision. The vertical incisions are made from the horizontal incision to the muco-gingival junction.

Next, a flap is created by peeling open the region of gum defined by the horizontal and vertical incisions, either in the upward direction for surgeries on the an upper tooth, or in the downward direction for a lower tooth, thus exposing the underlying bone. Then new tissues are grafted under the flap onto existing tissues. The new grafted tissues can come from the patient's own palate tissues, or from donor or animal tissues.

After the grafting of new tissues, the flap is closed down onto the grafted tissues, and the incisions are closed using multiple sutures.

While this surgery technique is capable of repairing gingival defects for one tooth or a group of adjacent teeth, it is a complicated surgery with a relatively long recovery time and significant morbidity. The outcome of the surgery is technique sensitive—the surgery is subject to failure from errors made by even well-trained surgeons or operators. Also, the incision area is large, which increases the recovery time and increases the possibility of an infection. Lastly, due to the large incisions made during the surgery and the grafting of new tissues, it is likely that the patient will have visible permanent scars on the gum tissues resulting from the surgery. In addition, the grafted tissue often does not match with the patient's own tissues in color and appearance, which may further create an unaesthetic appearance for the patient.

A second and less invasive surgery technique is also available to correct minor gingival defects. First, a small incision is made approximately 2-3 mm away from the receded gum line. Another incision is made at the gum line. A split-thickness dissection (operation to delicately "fillet" the inner side of the flap) is then performed. If not properly done, this dissection procedure can lead to a loss of blood supply and necrosis of the flap. When dissection is completed, this thinned out flap of gingival tissue is collapsed into the defect and held for a few minutes. Suturing is generally not necessary.

While this surgery technique is less invasive compared to the previous technique, there are several disadvantages. First, because part of the gum is moved to cover the gingival defect, this leaves a gap at the point of incision. This gap can expose part of the root of the tooth and may lead to other complications. Secondly, this technique allows at most a movement of the gum line for up to 3 millimeters (mm), and is not available for more severe gingival defects where the gum line recedes more. Further, this technique can be used to repair gingival defect for only one tooth at a time, not a group of teeth. Hence, each tooth with a gingival defect requires a separate incision. Like the previous technique, this technique can also leave unsightly permanent scars on the gum of the patient. Lastly, this technique is not recommended for operations on lower teeth.

The above-described surgical methods are typically executed using conventional instruments. The design of these instruments, in terms of size, blade design, angulations of connectors and other characteristics, require extensive incisions and intricate suturing techniques. These instruments are not designed for minimally invasive gingival or papillae augmentation surgeries. For example, a "Goldman Knife" is an angled dental surgery instrument, with a shaft, a curved connector section connecting to the shaft, and a protruding blade section, wherein the blade has a cutting surface perpendicular to the length direction of the connector section immediately connecting to it. Because this instrument and other conventional instruments are not designed in particular to be used for gingival or papillae augmentation surgeries, the use of these instruments require large incisions and awkward operating angles for the surgeon, increasing the recovery time for the patient and decreasing the success rate of the surgeries.

Therefore, because of the disadvantages and limitations of the conventional surgical methods described above, it is highly desirable to have a surgical method which enables the efficient correction of severe gingival defects of varying degrees with one minimally invasive incision. A minimally invasive technique can minimize bleeding, swelling, and other post operative symptoms. Furthermore, a technique that does not interrupt the blood supply from gingival and mucosal tissues promotes rapid healing and minimize chances of infection. In addition, a technique that requires no suturing of soft tissues saves the surgeon operating time and minimizes tissue trauma and patient discomfort. Also, a method that is not "technique sensitive", requiring no complex flap design and intricate suturing techniques, increases the success rate of the operation. It is also highly desirable to have a method that is effective in all four quadrants of the mouth, and applicable to large gingival defects, such as defects with recession of 7 mm or more in Miller I and II situations. Lastly, it is highly desirable to have a method that is cosmetically ideal and requires no tissue matching. In addition, it is also highly desirable to have instruments designed especially for performing gingival defect correction surgeries (gingival or papillae augmentation surgeries) with the characteristics described above to minimize the incision size and increase the surgeon's or operator's efficiency and success rate.

SUMMARY OF THE DISCLOSURE

Embodiments of the present invention relate generally to surgical methods of and surgical instruments for periodontal surgeries, such as a gingival or papillae augmentation operations, according to the Chao Trans-Mucosal and Papillae Elevation (TMPE) approach. Further, the embodiments of the surgical instruments have designs that minimize the size of the incision size and maximizes the efficiency of the operation.

A method of performing periodontal surgery to correct a gingival defect of a patient according to a general embodiment of the present invention comprises the steps of making an incision at or near a fornix of the patient near the gingival defect, inserting an instrument into the incision to detach a flap, extending the flap horizontally and vertically without enlarging the incision, elevating papillae within the flap, advancing the flap to cover the gingival defect, and pressing against the flap to promote fibrin formation.

In various embodiments of the method of performing periodontal surgery to correct a gingival defect, the incision is between 3-5 mm in length. In general embodiments of this method, no suturing is required. In various embodiments, the step of extending the flap horizontally further comprises extending the flap to cover a tooth immediately distal to the incision or a tooth immediately mesial to the incision. In various embodiments, the method of performing periodontal surgery further comprises the steps of determining whether the flap is stable, and performing papillary augmentation upon a determination that the flap is unstable.

An instrument for performing periodontal surgery according to one general embodiment comprises a handle, a first shank connecting to and extending from the handle, a connector section, and a blade section. In this embodiment, the connector section comprises a first end and a second end, wherein the first end connects to the first shank at a first angle, and the second end connects to the blade section at a second angle. Further, in this embodiment, the blade section comprises a cutting surface lying on a plane substantially parallel to a length direction of the second end of the connector section.

In various embodiments, each of the first angle and the second angle is approximately 90 degrees, and the connector section is substantially straight. In some embodiments, the first angle is approximately 90 degrees in the counter-clockwise direction, and the second angle is approximately 90 degrees in the clockwise direction. In some embodiments, the first angle is approximately 90 degrees in the clockwise direction, and the second angle is approximately 90 degrees in the counter-clockwise direction.

In various embodiments, the blade section is one of either a half-moon shape or a spear shape. In some embodiments, the blade section is 1-3 mm wide and has a sharp point and cutting edges on two sides. In some embodiments, the blade section is thin and needle-like. Further, in some embodiments, a tip of the blade section curves 10-30 degrees.

In various embodiments, the instrument is composed of one of either surgical-grade stainless steel, titanium, or titanium nitride. In some embodiments, the instrument further comprises a protectant coating. In some embodiments, the protectant coating is composed of Titanium-Nitride (TiN).

In various embodiments, the connector section is approximately 11 mm long, and the blade section is approximately 13 mm long. In some embodiments, the connector section is within a range of 4-18 mm long, and the blade section is within a range of 4-21 mm long.

In various embodiments, the connector section further comprises a second shank comprising the first end of the connector section connected to the first shank at the first angle, and a third shank comprising the second end of the connector section connected to the blade section at the second angle, wherein the second and third shanks adjoins and forms a third angle.

In some embodiments, the first angle in approximately 60 degrees, the second angle is approximately 90 degrees, and the third angle is approximately 60 degrees. In some embodiments, the first angle is approximately 100 degrees, the second angle is approximately 90 degrees, and the third angle is approximately 110 degrees. In some embodiments, the first angle is within a range of 10-90 degrees, the second angle is approximately 90 degrees, and third angle is within a range of 10-90 degrees. In some embodiments, the first angle is within a range of 90-135 degrees, the second angle is approximately 90 degrees, and the third angle is within a range of 90-135 degrees.

In some embodiments, the second shank is approximately 11 mm long, and the third shank is approximately 8 mm long. In some embodiments, the second shank is approximately 6 mm long, and the third shank is approximately 11 mm long. In some embodiments, each of the second shank and the third shank is within a range of 4-18 mm long.

BRIEF DESCRIPTION OF THE DRAWINGS

FIGS. 2A and 2B illustrate perspective views of the instruments 1A and 1B shown in FIGS. 1A and 1B;

FIGS. 4A and 4B illustrate perspective views of the instruments 2A and 2B shown in FIGS. 3A and 3B;

FIGS. 6A and 6B illustrate perspective views of the instruments 3A and 3B shown in FIGS. 5A and 5B;

FIGS. 10A and 10B illustrate perspective views of the instruments 5A and 5B shown in FIGS. 9A and 9B;

DETAILED DESCRIPTION OF PREFERRED EMBODIMENTS (1) Surgical Techniques for Gingival Augmentation The Chao Trans-Mucosal and Papillae Elevation Approach (Chao TMPE approach) is a technique requiring a minimal incision but capable of performing gingival or papillae augmentation at multiple sites. The Chao TMPE approach is a method capable of repairing gingival defects in all four quadrants of the mouth, and is predictably effective for defects up to 7 mm and defects larger than 7 mm in Miller I, II classification of root defects.

Figure 15:
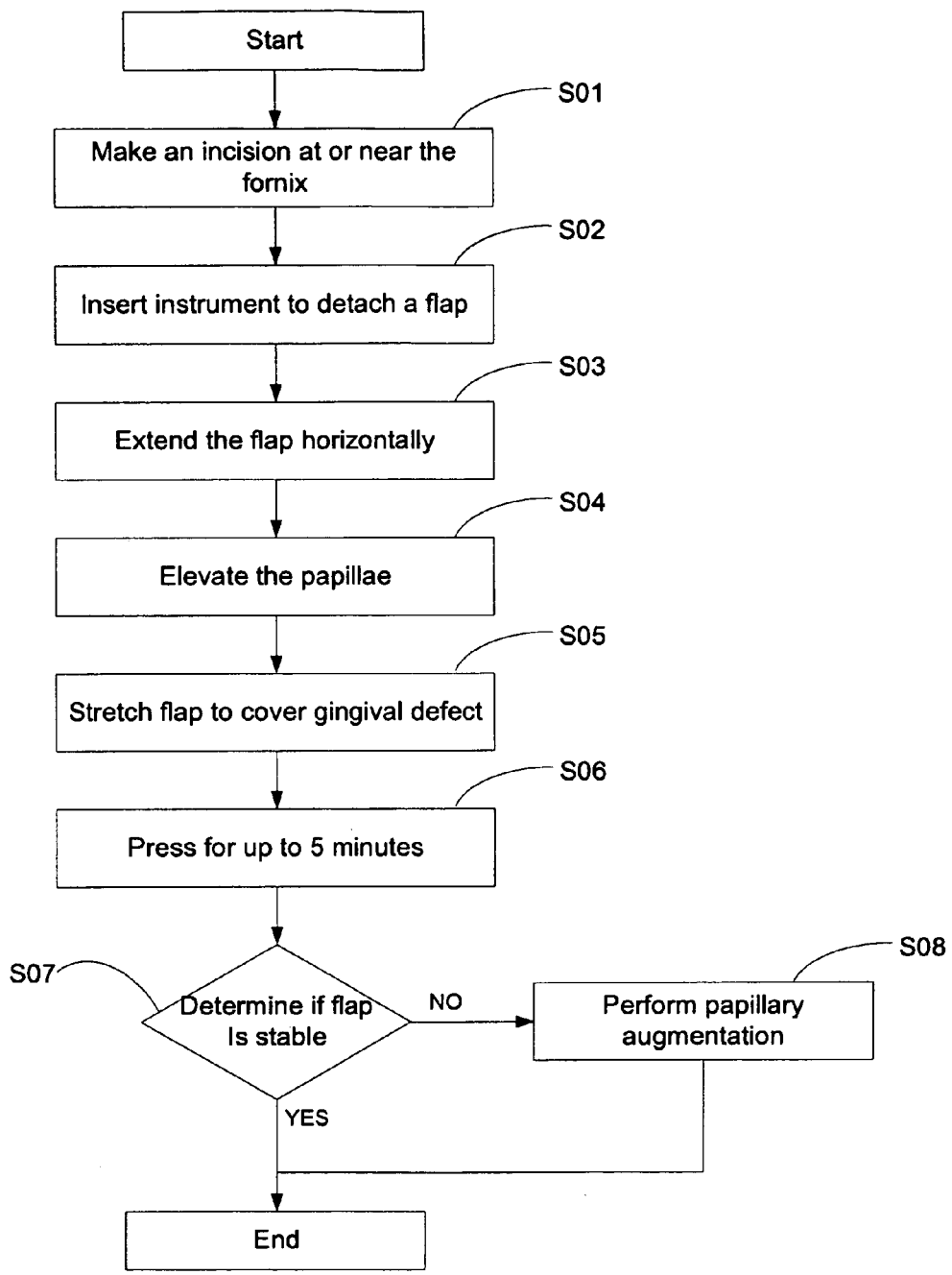
FIG. 15 is a flow-chart illustrating the steps of performing a gingival or papillae augmentation surgery according to one preferred embodiment; and, FIGS. 16(a) and 16(b) illustrate the step of extending a flap horizontally without enlarging the incision, according to one preferred embodiment.

FIG. 15 is a flow-chart illustrating the steps of performing a gingival or papillae augmentation surgery in accordance with the Chao TMPE approach, according to one preferred embodiment. First, as shown by step S01 of FIG. 15, the Chao TMPE approach involves making a horizontal minimal incision of approximately 3-5 millimeters (mm) at or near the fornix (depth of the bucco-muccal fold). This incision can be made using a standard dental surgical instrument such as, but not limited to, a scalpel. The incision is practically invisible because of its small size and its location far away from the visible gum line. TMPE instruments, which are discussed in detail later, are designed so that generally only one incision of 3-5 mm is needed for up to three gingival defects. If more than three gingival defects are being treated, another 3-5 mm incision can be made two or more teeth away from the first incision point. A more experienced operator will be able to routinely utilize an incision of 3 mm, whereas a less experienced operator may require up to 5 mm for each incision. Where there are two adjacent defects, the incision should be made at the fornix between the buccal roots of the two teeth. Where there are three adjacent defects, the incision should be made near the root of the tooth in the center. Where there are four or more adjacent defects, two incisions should be made. When making two adjacent incisions to correct four adjacent defects, the mesial incision should be made between the two most mesial roots and the second incision should be made between the two most distal roots. When making the incision, the angle of the blade of the TMPE instruments, which are discussed in detail later, should be approximately at 90 degrees to the underlying bone. It is noted that while the minimum incision required for this procedure is between 3-5 mm in length, this procedure is applicable for incisions longer than 5 mm.

Next, as shown by step S02, the appropriate surgical instrument is inserted to detach a flap and extend the flap vertically. Next, the flap is extended horizontally (FIG. 15, step S03). Then, the papillae surrounding the effected tooth is elevated (FIG. 15, step S04). Making the incision at the fornix allows maximum "give" or room to move the aperture mesially (closer to the middle of the front of the jaw) and distally (away from the middle of the front of the jaw) for the release of the flap and papillae (the gum tissue between two neighboring teeth).

To detach a flap (FIG. 15, step S02), the appropriate TMPE instruments, as discussed in detail later, is introduced through the incision pointing in the coronal direction (towards the crown of the tooth). The blade of the TMPE instrument is placed at an acute angle onto the bony surface. With a slicing action the blade is pressed coronally to separate the mucosal and gingival tissue from their bony attachments. Care should be taken not to perforate the flap. This is accomplished by keep the blade angled towards and pressed against the bone. By increments the flap is released from the underlying bone. A connective tissue nodule is often encountered between the upper anterior teeth. This nodule is generally located between the roots near the muco-gingival junction. Since this nodule has not been described in the literature, the nodule is called the Chao Nodule. Special care should be taken to undermine the Chao Nodule with a slicing motion of the blade without perforating the flap.

In extending the flap horizontally (FIG. 15, step S03), the flap should extend distally well beyond the distal papillae of the tooth immediately distal to the tooth or group of teeth being treated, and mesially well beyond the mesial papillae of the tooth immediately mesial to the tooth or group of teeth being treated. Vertically this flap should extend from the incision to the gingival margin of the treated tooth and the teeth adjacent to it. By using the appropriate TMPE instruments, the flap can be extended horizontally without increasing the size of the initial 3-5 mm incision. Careful use of the appropriate instrument can avoid causing perforations to the flap or injuries to the root or implant surfaces while at the same time negating the need for any additional gingival incisions. Before proceeding further, the operator should ascertain that all ligaments or tissues are complete detached from the flap. The completely loosened flap allows convenient access to all papillae.

Figure 16A:
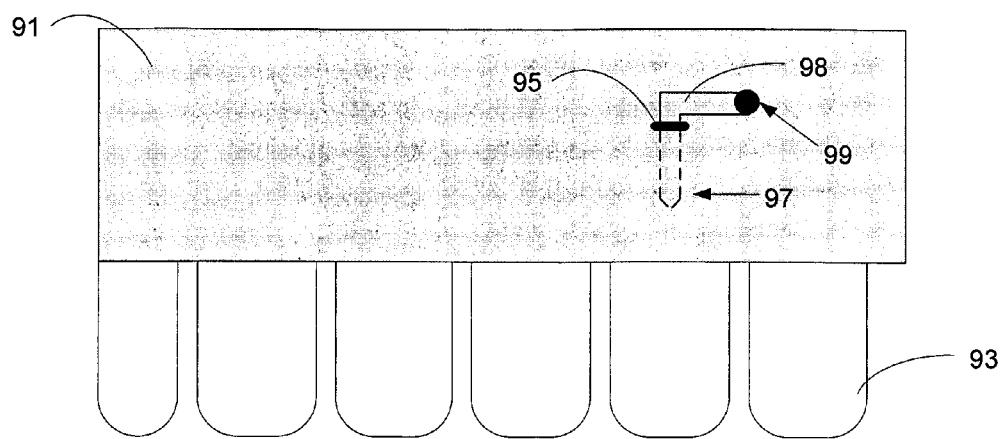
Figure 16B:
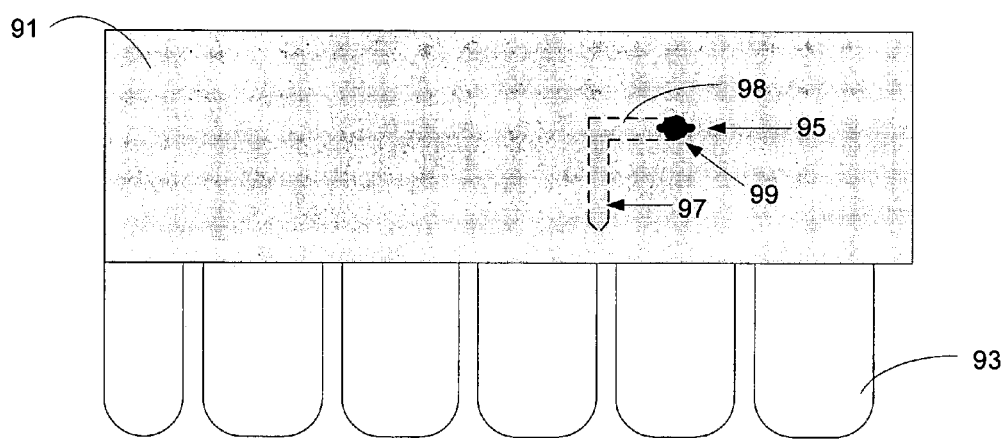

FIG. 15 is a block diagram further illustrating the detaching and horizontal extension of the flap according to steps S02-S03 of FIG. 15. It is noted that FIG. 15 is a block diagram illustrating the concept of the operation only; therefore the shapes and geometries are not drawn to scale. In FIG. 16(a), an incision 95 of 3-5 mm is first made on the gum 91 above a group of teeth 93. Next, the blade section 97 of an instrument is inserted through the incision 95. The instrument comprises at least a blade section 97 and a connector section 98. The remainder of the instrument 99 is at an angle with respect to the plane of the drawing of FIG. 16(a), and is not illustrated. In FIG. 16(a), the portion of the instrument submerged beneath the surface of the gum tissue is illustrated by dashed lines. In FIG. 16(a), as the blade section 97 extends downwards, the flap is extended vertically. FIG. 16(b) illustrates the position of the instrument after a horizontal extension of the flap, when the lateral component (connector section 98) is extended through the incision 95 in a leftward direction with respect to its position in FIG. 16(a), without enlarging the size of the incision 95. Depending on the length of the connector section 98 of the instrument, the horizontal extension of the flap can reach at least the tooth adjacent to the incision and possibly further. However, in order to achieve this horizontal extension, the plane the cutting surface of the blade section 97 lies on must be substantially parallel to the connector section 98 immediately connecting to the blade section 97. Currently, instruments that satisfy this criteria cannot be found on the market. For example, the "Goldman Knife" has a blade section with a cutting surface perpendicular to the connector section, which prevents the horizontal extension of the flap through the same incision. The Chap TMPE instruments, which are discussed in detail later, are specially designed to be used in this method.

Next, the appropriate Chao TMPE papillae elevators, as discussed in detail later, can be used to carefully elevate and detach the papillae (FIG. 15, step S04) from the roots (hereafter roots refer to natural roots as well as implants or their abutments) and the underlying bone. Papillae elevation should extend as lingually as possible, without cutting or unnecessarily traumatizing the papillae. Any cutting of the papillae may result in the inability to augment the flap properly. This can also lead to subsequent shrinkage of the papillae. When an atraumatic elevation of the papillae is accomplished, the result is that the entire gingival flap is mobile and can be easily moved coronally. The Chao TMPE papillae elevator instruments, as discussed in detail later, are also designed to reach the papillae distal to or mesial to the incision without enlarging the incision.

Next, the flap is advanced coronally with gentle digital pressure until the gingival defect is completely covered (FIG. 15, step S05). The operator may further "stretch" the flap by using one finger to press the flap against the root while another finger pushes and stretches the bucc-mucal fold, then release digital pressure. The flap tissue over the gingival defect is then pressed gently for up to five minutes to promote fibrin formation (FIG. 15, step S06).

Next, the operator can determine if the flap is stable (FIG. 15, step S07). The determination whether the flap is stable (FIG. 15, S07) can be accomplished by checking if the defect remains covered by the flap when the mucosa is pulled apically or horizontally. If the defect remains covered, then the flap is stable (FIG. 15, S07:YES), and the surgical aspect of the procedure is finished. No further steps, such as suturing, is necessary. The patient can be dismissed with proper instructions. Typically, the 3-5 mm initial incision heals within the span of less than one week.

In some cases where the flap is unstable (FIG. 15, S07: NO), papillary augmentation (FIG. 15, step S08) with resorbable collagen membraneous graft material may be used. The graft material (Biogide is recommended) may be rolled or cut into a triangular shaped pieces, or any other convenient shape, that fits into the triangular space under the papilla. This material is then inserted via the incision with gentle pressure under the papilla with un-serrated cotton pliers. Then the appropriate papillae elevator is used to "tug" the graft snugly under the papilla. This is repeated for all the papillae needing augmentation. Tugging the graft material underneath the papillae will generally stabilize both the graft material and the flap. Tugging the mucosa, cheek or lip should not result in any movements of the flap. If movement is observed, the operator should re-examine the flap to see whether all ligamentous and tissue attachments have been severed from the flap. When thoroughly released from the roots and bone, the flap will likely remain immobile. Pressing the flap over the root defect for up to five minutes will assure fibrin formation and end the procedure.

In summary, the result of the method illustrated in FIG. 15 is the coverage of the gingival defect with a technique that requires only one 3 mm-5 mm practically invisible incision, with no suturing of the patient's oral tissue required. As a result of the minimal incision size and lack of suturing, the bleeding and swelling of the gum is kept to a minimum and thus recovery of the patient is accelerated. Often, the patient will see that the gums appears to have grown over the defect in just one appointment. Due to the vascularity and collagenous nature of mucosal tissue, healing of the incision is rapid and generally the incision becomes virtually undetectable within a week. Post-operative symptoms are minimal and generally require no more than one or two over-the-counter NSAIDS (Non-Steroidal Anti-Inflammatory Drugs).

It is recommended, whenever feasible, to perform dentinoplasty as part of root preparation. The performance of dentioplasty appears to allow easier advancement of the flap, as well as allow better long term stability of the re-attachment.

(2) Osseous Surgery Using the Chao TMPE Approach

The incision technique described above, as well as the surgical instruments discussed in detail later, can also be used to perform osseous surgery. For purposes of osseous surgery, the Chao TMPE approach to flap and papillae elevation as described above allows access to the bony defect through the mucosal incision. The incision may need to be extended to allow sufficient reflection of the flap to allow direct visualization of the bony defect from the labial or buccal aspect of the bony defect. This approach will minimize gingival recession, which is associated with techniques that call for labial or buccal gingival marginal incision. Furthermore, grafting is simplified because graft materials can be inserted underneath the papillae and flap, often without the need for suturing. The clinician does not have to be concerned with the complete enclosure of the graft material by the flap. Since blood supply to the grafted area remains relatively uncompromised, healing is accelerated compared to techniques that employ gingival incisions. Specially designed ultrasonic instruments can access mesial and distal bony pockets for root planning purposes. Placing bone graft and membranes can be accomplished with the Chao TMPE elevator instruments, which are discussed in detail below.

For buccal furcation of mandibular or maxillary molars the Chao TMPE approach allows for the buccal gingival margin to be so slackened such that gentle retraction of the flap from the buccal wall allows full access to the furcation from the buccal perspective. Advancing the flap coronally to give full coverage to the furcation area is not particularly technically challenging, even where gingival recession has exposed the furcation. Shrinkage and resorption of the flap over the buccal furcation is minimal because blood supply is not compromised by gingival incisions. This flap conveniently gives coverage to the graft materials and membranes which often does not need to be sutured. The ends of the membrane that covers the buccal furcation can be tugged under the mesial and distal papillae that stabilization is obtained without suturing. If suturing is desired, a simple sling suture engaging the graft membrane under the mesial and distal papillae of the tooth will stabilize the graft.

(3) Papillae Regeneration or Augmentation Using the Chao TMPE Approach

The incision technique described above, as well as the surgical instruments discussed in detail later, can also be used in papillae regeneration or augmentation. Papillae regeneration or augmentation may be accomplished by the Chao TMPE approach as described above. The use of an autogenous graft or membranous allograft (Alloderm) is recommended. By using Alloderm, or alternatively an autogenous graft, and stabilization using the Chao suturing technique, there is a higher likelihood of a predictably successful outcome compared to conventional methods. The reason for this higher success rate is that this approach leaves blood supply for the papillae and the gingival apparatus virtually unimpaired. Until now, other conventional papilla regeneration techniques have not been deemed predictably successful because of the need to make multiple incisions in the gingival region and the inability of current techniques to augment and elevate the papillae without restricting blood supply.

One alternative method for papillae augmentation (FIG. 15, step S08) is to cut a section of an acelluar dermal matrix allograft (Alloderm) into a U-shaped configuration. With a unique suturing technique described below, each end of this membrane is then tugged snugly under the mesial and distal papillae, with the middle segment overlying the gingival defect. The Chao TMPE allograph or autogenous graft (from the patient) suturing technique, with three variations, is described in the following paragraphs.

In a first variation of the Chao TMPE suturing technique, a U-shaped section approximately half the circumference of the root at the cemento-enamel junction (neck of the tooth) and at least 3 mm in width is cut from the Alloderm specimen. (Alternatively, connective tissue from another part of the mouth can be used.) The needle of a resorbable suture (Dexon or Chromic Catgut) with ½ round point (26.19 mm) is first threaded from the lingual through the mesial interproximal space, without piercing the papilla. Then the needle is threaded under the gingival margin, through the flap to appear at the horizontal incision. Next, the needle is made to engage one end of the U-shaped graft. It is suggested that the graft be placed against the convex surface of the end of a periosteal elevator or tissue retractor held firmly at the other end by a dental assistant while threading the needle through the graft, with the needle pointing away from the fingers of the operator. This will enhance the ease of accomplishing this procedure as well as protect against an exposure (puncture) incident.

Then the needle is threaded under the flap to appear at the gingival margin (gum line) without engaging the flap in any way. Next, the needle is threaded through the mesial interproximal space to the lingual of the tooth. From the lingual the needle is passed through the distal interproximal space without engaging the papillae, to appear on the facial side. The needle is next threaded under the flap to appear at the horizontal incision. Then the needle is made to puncture and thread through the other end of the U-shaped graft with the use of the convex surface of an instrument. With the specimen thus engaged by the suture (as if pulled by a sling from each end), the needle is thread under the flap, then passed through the distal interproximal space to reappear at the lingual. Then as both ends of the suture are pulled, the graft is pulled under the flap to rest against the root, with each end tugged under a papilla.

Next, The flap should be elevated by digital pressure to cover the defect before the suture is tightened. The graft material should remain under the flap, and not be squeezed over the gingival margin. Careful effort must be made to push any excess graft material under the flap. The knot can be tied at the lingual. This suturing will tightly attach the graft against the root defect while elevating and stabilizing the entire gingival apparatus (the flap and the papillae) at the desired position. At the operator's choice, the ends of the suture can be threaded under the opposite interproximal space and the knot then can be tied at the labial. A lingual knot makes the suture invisible, while presenting the patient with a possible annoyance to the tongue. A facial or labial knot may be visible to the eye and possibly displace the gingival margin of the flap.

When the distal and mesial papillae of the treated tooth and the papillae of the adjacent teeth have both been augmented by the graft material, the flap should now be relatively immovably fixated over the defect. Pulling or tugging the cheek, lip or mucosal tissue should not be result in any observable movement in the flap. It should be noted that in some circumstances the specimen may be "tugged" under the papillae without suturing. However, dislodgement may still be possible.

A second variation of the Chao TMPE graft suturing technique is described as follows. In this variation, the operator may use a double ended needle. As above, a U-shape configuration of the graft is cut that approximates the facial circumference of the neck of the tooth. Each end is threaded from the lingual to the facial, passed under the flap to appear at the horizontal incision, without engaging tissue. Then each needle is made to engage each end of the graft, and then passed through to the lingual without engaging any part of the flap. The knot is then tied at the lingual, or wrapped around the lingual and tied at the labial. Although this method appear easier to visualize, the surgeon will, with experience, probably find that using a single needle suture as described under the first variation of the suturing method to be simpler and easier.

In a third variation of the suturing technique, the U-shaped graft material is tugged underneath each papilla. With finger pressing against the graft just apical to the mesial papilla, a needle is made to pass from the outer surface of the flap, through the graft under the papilla, to appear at the lingual side. Then, the needle is wrapped around the root to the distal, and threaded through the distal interproximal space to appear on the facial side, without engaging any tissue. Next, with the finger pressing the graft against the distal papilla, the needle is made to engage the graft underneath the papilla from the facial aspect of the flap to emerge on the lingual side of the tooth. Next, the suture is passed through the mesial interproximal space to appear on the facial side of the tooth. The knot is then tightened and tied at the facial side.

According to the Chao TMPE approach, the papillae is loosened by disengaging the flap and the papillae from the root and the bone with only one incision that is remote from the papillae. Then, this technique calls for the stabilization of the elevated papillae by the insertion of an autogenous graft or Alloderm, without restricting blood supply from surrounding tissue. Current conventional methods call for the external suturing of the papillae after elevation and thus limits blood supply, resulting in less predictable results. The unique Chao papillae regeneration technique assures a high, predictable success rate, when performed as described above.

(4) The Surgical Instruments

The Chao TMPE (Trans-mucosal and Papillae Elevator) instruments are instruments designed to be used in the performance of the surgeries and operations discussed above. The TMPE instruments are specially designed to allow the operator to elevate, without direct vision, a full-thickness flap through the access provided by a minimal incision of 3-5 mm. This reflection of the flap is done in a unique way, i.e., the operator cannot directly see the tip of the elevator at any time during the procedure. The operator must deduce the location of the blade by the inflated shape and movement the elevator traces underneath the mucosa or gingiva. The design of the instruments facilitates the unique techniques discussed above. Depending on which quadrant of the patient's mouth the surgery is being performed, different TMPE instruments can be used.

Figures 1A, 1B:
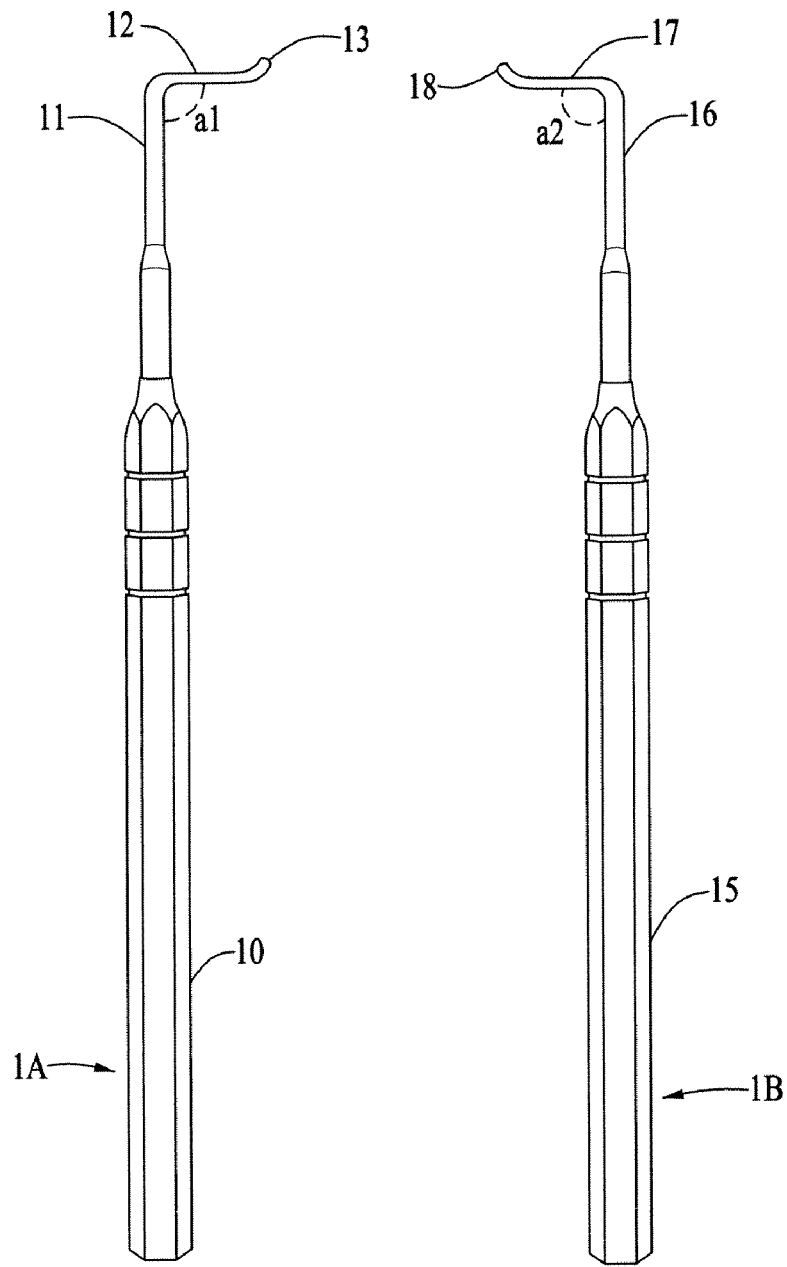
FIGS. 1A and 1B illustrate top views of Chao TMPE (Trans-mucosal and Papillae Elevator) instruments, according to one preferred embodiment.
Figure 3A:
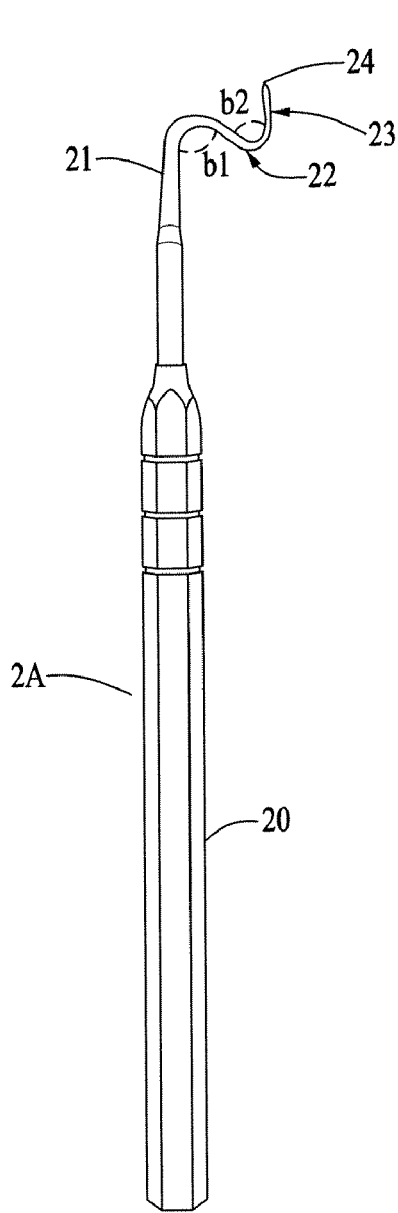
FIGS. 3A and 3B illustrate top views of Chao TMPE instruments 2A and 2B, according to another embodiment.
Figure 3B:
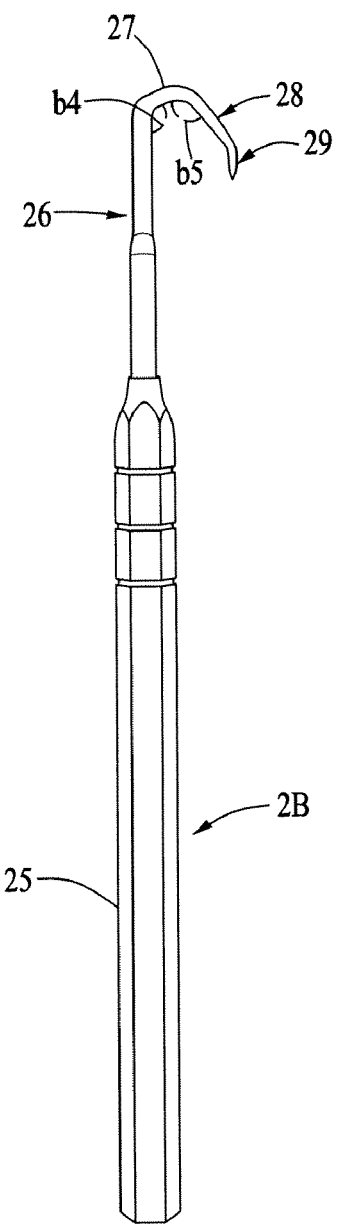
Figure 5A:
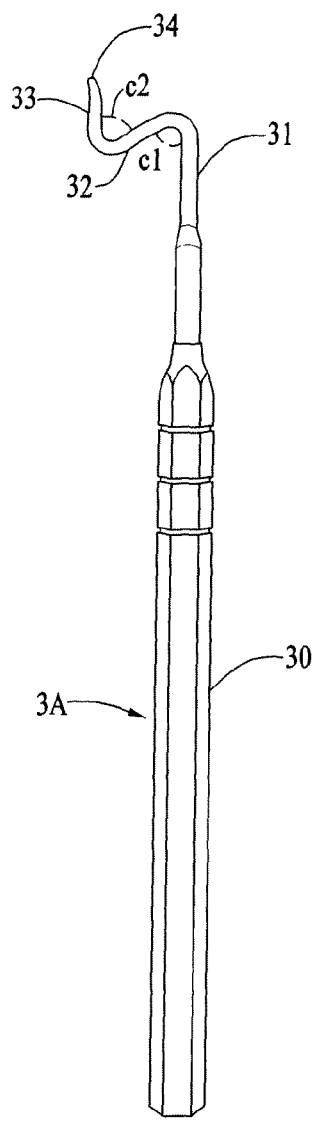
FIGS. 5A and 5B illustrate top views of Chao TMPE instruments 3A and 3B, according to yet another embodiment.
Figure 5B:
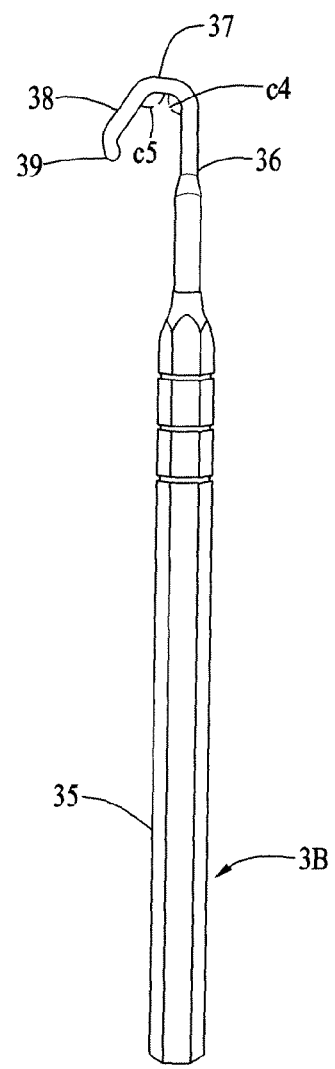
Figure 7A:
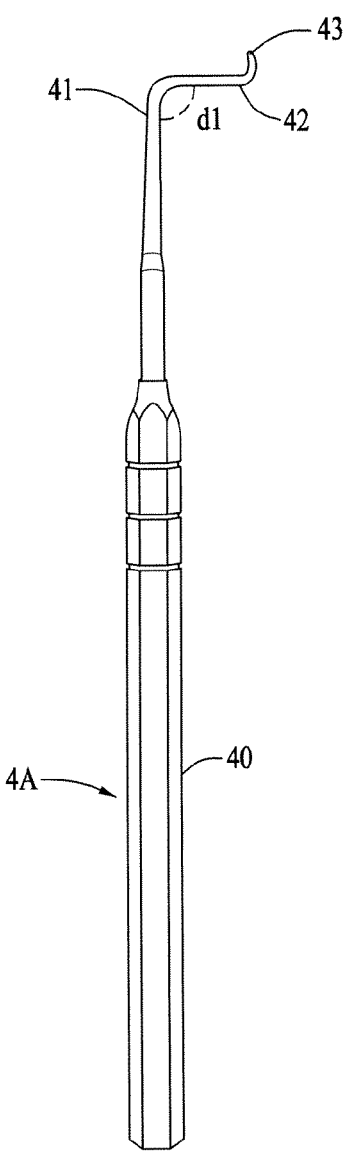
FIGS. 7A and 7B illustrate top views of Chao Papillae Elevator instruments 4A and 4B, according to yet another embodiment.
Figure 7B:
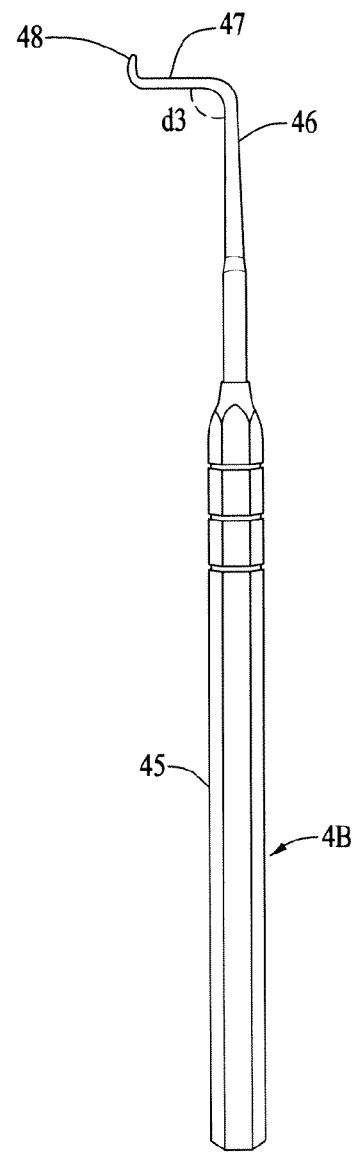
Figures 8A, 8B:
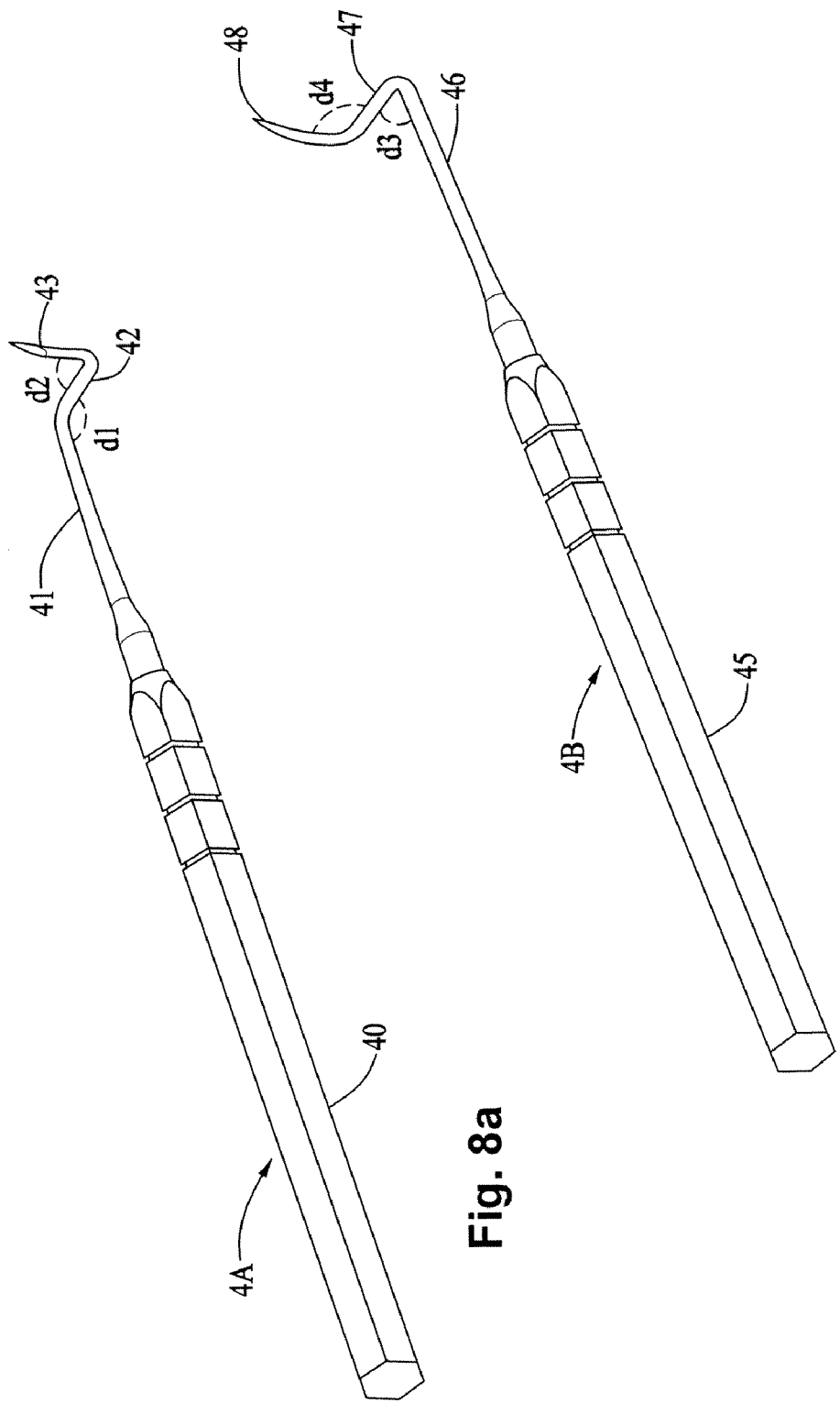
FIGS. 8A and 8B illustrate perspective views of the instruments 4A and 4B shown in FIGS. 7A and 7B.
Figure 9A:
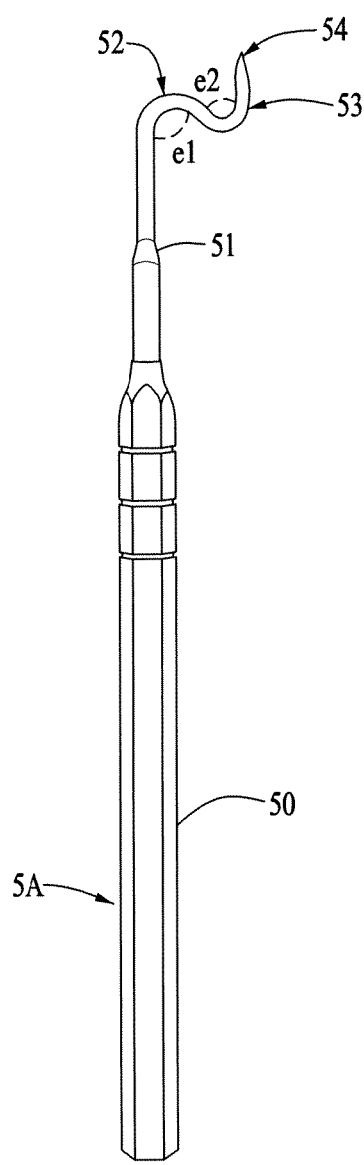
FIGS. 9A and 9B illustrate top views of Chao Papillae Elevator instruments 5A and 5B, according to yet another embodiment.
Figure 9B:
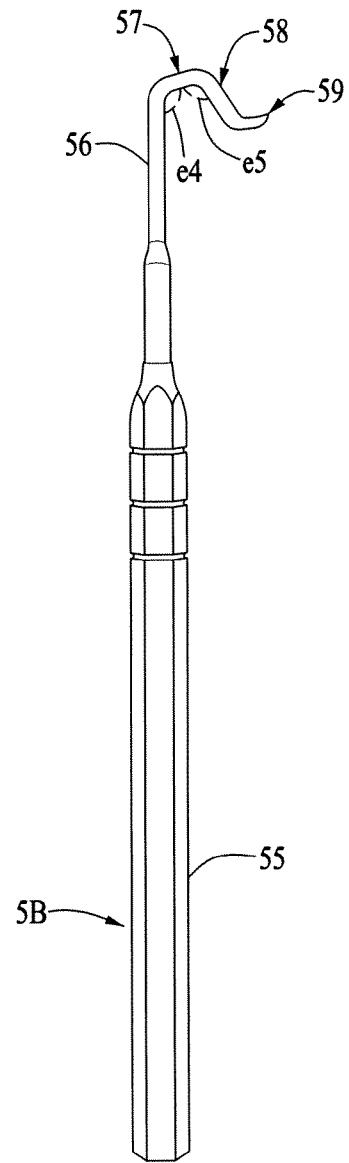
Figure 11A:
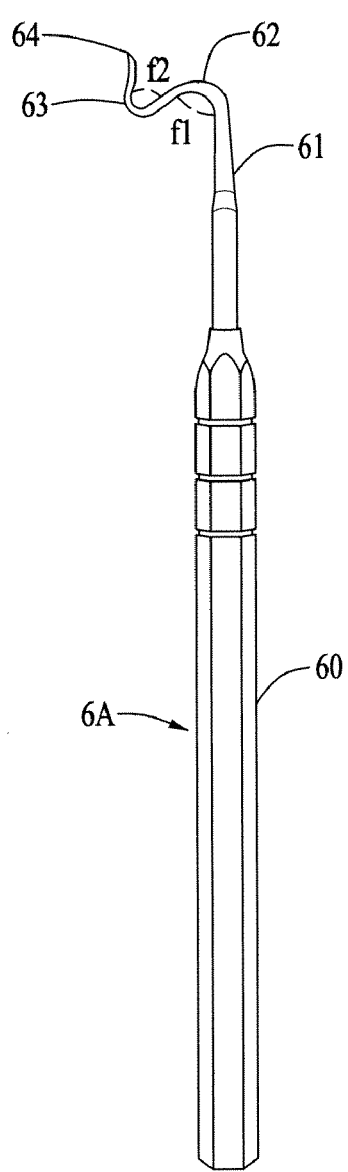
FIGS. 11A and 11B illustrate top views of Chao Papillae Elevator instruments 6A and 6B, according to yet another embodiment.
Figure 11B:
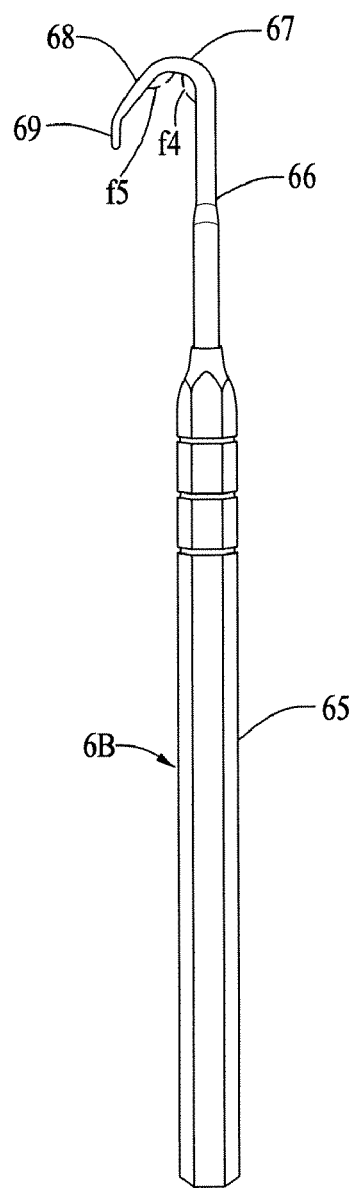
Figures 12A, 12B:
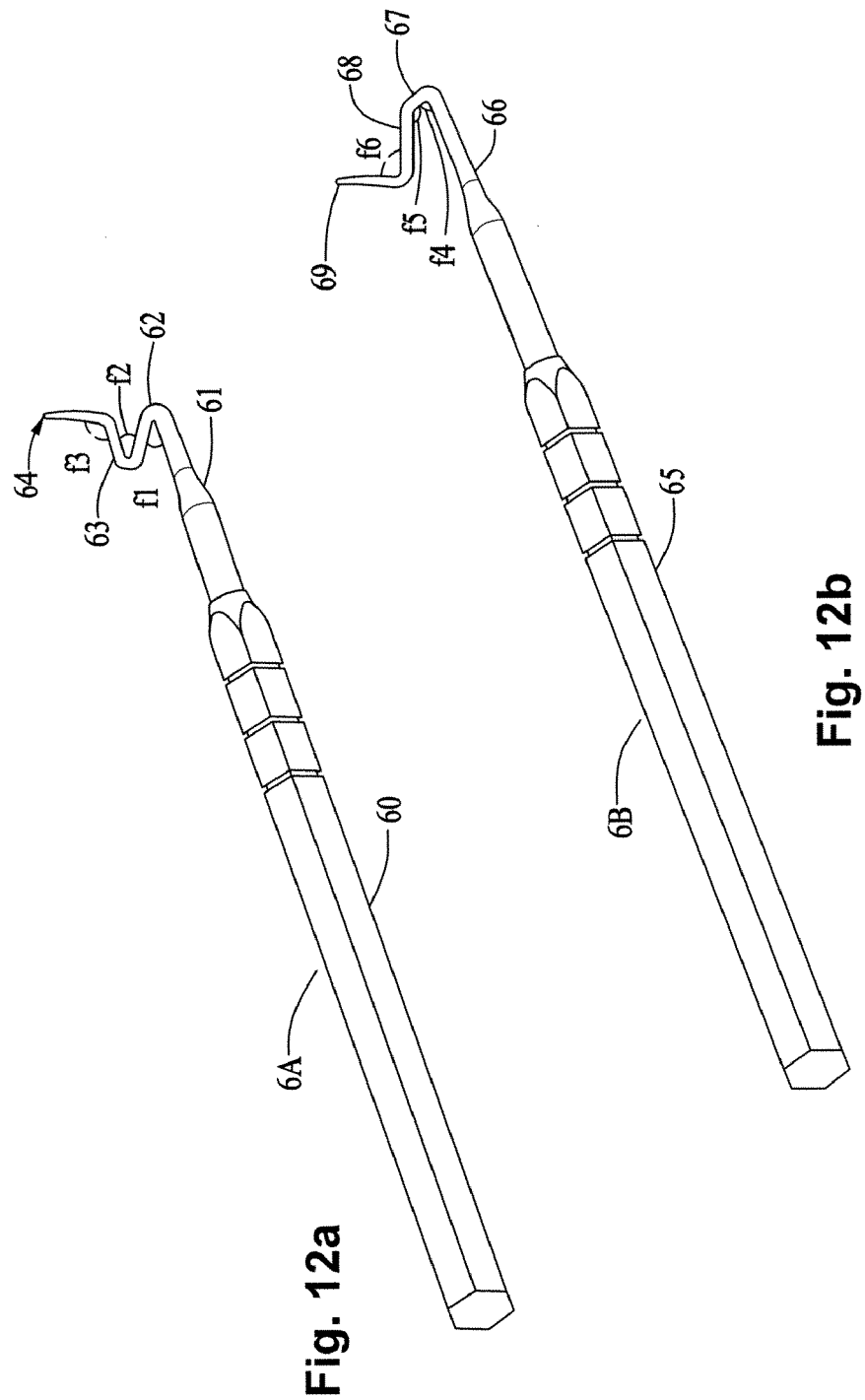
FIGS. 12A and 12B illustrate perspective views of the instruments 6A and 6B shown in FIGS. 10A and 10B.

FIGS. 1A, 1B, 2A, and 2B illustrate a first set of embodiments of the Chao TMPE (Trans-mucosal and Papillae Elevator) instruments that can be used to perform the surgeries and operations discussed above. FIGS. 1A and 1B show a top view of a set of instruments 1A and 1B, and FIGS. 2A and 2B show a perspective view of the same set of instruments. These two instruments 1A and 1B may be also called the Chao TMPE Universal instruments.

As shown in FIGS. 1A, 1B, 2A, and 2B, TMPE instrument 1A is an instrument with a handle 10, a first shank 11 linearly extending from the handle 10, a second shank 12 connected to the first shank 11 at one end and rotated at an angle a1 from the first shank 11 in the counter-clockwise direction, and a blade section 13 rotated at an angle a3 from the second shank 12 in the clockwise direction and connected to a second end of the second shank 12.

Also shown in FIGS. 1A, 1B, 2A, and 2B, TMPE instrument 1B is an instrument with a handle 15, a first shank 16 linearly extending from the handle 15, a second shank 17 connected to the first shank 16 at one end and rotated at an angle a2 from the first shank 15 in the clockwise direction, and a blade section 18 rotated at an angle a4 from the second shank 17 in the counter-clockwise direction and connected to a second end of the second shank 17.

For TMPE instrument 1A and 1B, the second shanks (12 and 17) act as connector sections that connect the blade sections (13 and 18) to the handles (10 and 15) and first shanks (11 and 16).

As illustrated in FIGS. 1A, 1B, 2A, and 2B, TMPE instruments 1A and 1B have generally the same shape and design, but differ in the rotational direction of the second shanks (12 and 17) with respect to the first shanks (11 and 16), and the rotational direction of the blade sections (13 and 18) with respect to the second shanks (12 and 17). TMPE instruments 1A and 1B are essentially "mirror images" of each other, when viewed along a line parallel to the length direction of the handles 10 and 15.

As illustrated on FIGS. 1A, 1B, 2A, and 2B, the angles a1, a2, a3, and a4 are all approximately 90 degrees. Further, for TMPE 1A, the blade section 13 is orthogonal to a plane formed by the length direction of the first shank 11 and the length direction of the second shank 12. In other words, the length direction of the blade section 13 is perpendicular to the length directions of both the first 11 and the second 12 shanks. Likewise, for TMPE 1B, the blade section 18 is orthogonal to a plane formed by the length direction of the first shank 16 and the length direction of the second shank 17.

While the embodiments illustrated in FIGS. 1A, 1B, 2A, and 2B have the angles a1, a2, a3, and a4 at approximately 90 degrees, it is not necessary for these angles to be exactly 90 degrees. Instruments according to other embodiments have angles substantially close to but not exactly 90 degrees, up to a variation of +/−10 degrees from 90 degrees, that accomplish the same results.

In one embodiment, the second shanks (12 and 17) for TMPE 1A and 1B are each 11 mm long. However, other embodiments could have the second shank varying in length. In various embodiments, the lengths of the second shank (12 or 17) could vary from 4 mm to 18 mm for instruments 1A and 1B.

In one preferred embodiment, each of the blade section (13 and 18) for TMPE 1A and 1B is approximately 13 mm long. The length of the blade section (13 or 18) could vary depending on the tooth and gum dimensions of the patient. Some embodiments have a shorter blade section of 4 mm, some embodiments have a longer blade section of 21 mm, and some embodiments have blade sections varying between 4-21 mm. The width of the blade section could also vary from 1 mm to 3 mm. The width of the blade section limits the incision of the Chao TMPE Approach to about 3-5 mm. Further, as illustrated in FIGS. 2A and 2B, the width directions of the blade sections 13 and 18 are substantially perpendicular to the length direction of the handles 10 and 15, respectively. In other words, the planes of the cutting surfaces of the blade sections 13 and 18 are each substantially parallel to the second shanks 12 and 17. As discussed above, this allows the blade section to expand the flap horizontally without increasing the incision size. Because the second shanks (12 and 17) are parallel to the planes of the cutting surfaces, they can be submerged under the flap through the incision during the horizontal extension of the flap as illustrated in FIG. 16. This cannot be accomplished with any convention instruments on the market today.

In addition, each of the blade sections (13 and 18) could also vary in shape. For example, the blade could be basically round with a cutting edge formed by flattening of one surface (half-moon shaped), or a double-edged blade (spear-shaped).

Using TMPE instruments 1A or 1B, the operator or surgeon can insert the sharp tip of the blade section 13 or 18 into an incision of 3-5 mm (FIG. 15, S01). Pressure is applied, according to the techniques detailed above in section (1), such that the blade section (13 or 18) of TMPE 1A or 1B slices under the mucosa or gingival, detaching a flap (FIG. 15, S02). Next, the blade section can be moved laterally to extend the flap horizontally to the teeth adjacent to the incision (FIG. 15, S03). As illustrated in FIGS. 16(a) and 16(b), during the horizontal extension of the flap, the lateral component of instruments 1A or 1B, the second shanks 12 or 17, becomes submerged under the gum through the incision point. Hence, the "reach" of instruments 1A or 1B is determined by the length of the second shanks 12 or 17.

Using the techniques described above and in earlier sections, TMPE 1A can be used to reflect the flap distally in the in the upper right and lower left quadrants of the patient's mouth. TMPE 1A can also be used to release the flap mesially in the upper left and lower right quadrants. TMPE 1B is an instrument that can used to release the flap mesially in the upper right and lower left quadrants of a patient's mouth. TMPE 1B can also be used to release the flap distally in the lower right and upper left quadrants.

When using TMPE instrument 1A or 1B, the operator may find that when treating posterior teeth, the movement of the instrument is impeded by the handle impinging the cheek or the corner of the mouth. As shown in FIGS. 3A, 3B, 4A, 4B, 5A, 5B, 6A, and 6B, TMPE instruments 2A, 2B, 3A, and 3B are instruments designed in a manner that the handle is angled mesially away from the corner of the mouth. The angled design allows the blade section of the instrument to reach under the flap and access mesial and distal aspects of the flap without hindrance from facial structures. Hence, instruments 2A, 2B, 3A, and 3B can reach posterial surgical sites, e.g., buccal to second bicuspids or first molars, without impinging the patient's facial features. Further, "bends" in the design of the shanks allow the surgeon to apply a controlled force to elevate the attached gingiva.

As illustrated in FIGS. 3A, 3B, 4A, and 4B, 2A and 2B are a second set of embodiments of TMPE instruments. TMPE instrument 2A comprises a shaft 20, a first shank 21 extending linearly from the shaft 20, a second shank 22 connected to the first shank 21 on one end and rotated from the first shank 21 at an angle b1 in the counter-clockwise direction, a third shank 23 connected to a second end of the second shank 22 and rotated from the second shank 22 at an angle b2 in the clockwise direction, and a blade section 24 connected to the third shank 23 rotated at an angle b3 from the third shank 23 in the clockwise direction.

Also illustrated in FIGS. 3A, 3B, 4A, and 4B, TMPE instrument 2B comprises a shaft 25, a first shank 26 extending linearly from the shaft 25, a second shank 27 connected to the first shank 26 on one end and rotated from the first shank 26 at an angle b4 in the counter-clockwise direction, a third shank 28 connected to a second end of the second shank 27 and rotated from the second shank 27 at an angle b5 in the counter-clockwise direction, and a blade section 29 connected to the third shank 28 rotated at an angle b6 from the third shank 28 in the clockwise direction.

For TMPE instrument 2A and 2B, the second shanks (22 and 27) and third shanks (23 and 28) act as connector sections that connect the blade sections (24 and 29) to the handles (20 and 25) and first shanks (21 and 26).

FIGS. 3A, 3B, 4A, and 4B illustrate one preferred embodiment of TMPE 2A where the angle b1 is approximately 60 degrees, the angle b2 is approximately 60 degrees, and the angle b3 is approximately 90 degrees. In other embodiments, any reasonable angle from 10-90 degrees for each of the angles b1 and b2 also could also work. As shown in FIG. 4, the angle b3 is approximately 90 degrees, but it is not necessary to be exactly 90 degrees. The angle b3 could vary within +/−10 degrees of 90 degrees. The length directions of the first 21, second 22, and third 23 shanks are coplanar. The length direction of the blade section 24 is approximately orthogonal to the plane formed by the length directions of the first 21, second 22, and third 23 shanks.

Likewise, FIGS. 3A, 3B, 4A, and 4B also illustrate one preferred embodiment of TMPE 2B where the angle b4 is approximately 100 degrees, the angle b5 is approximately 110 degrees, and the angle b6 is approximately 90 degrees. In other embodiments, any angle larger than or equal to 90 degrees but smaller than 135 degrees for b4 could also work, and any angle larger than or equal to 90 degrees but smaller than 135 degrees for b5 could also work. As shown in FIG. 4, the angle b6 is approximately 90 degrees, but could also be within +/−10 degrees of 90 degrees. The length direction of the first 26, second 27, and third 28 shanks are coplanar. The length direction of the blade section 29 is approximately orthogonal to the plane formed by the length directions of the first 26, second 27, and third 28 shanks.

For one embodiment of TMPE 2A as illustrated in FIGS. 3A, 3B, 4A, and 4B, the length of the second shank 22 is approximately 11 mm, the length of the third shank 23 is approximately 8 mm, and the length of the blade section 24 is approximately 13 mm. For the embodiment of TMPE 2B shown in FIGS. 3A, 3B, 4A, and 4B, the length of the second shank 27 is approximately 6 mm, the length of the third shank 28 is approximately 11 mm, and the length of the blade section 29 is approximately 13 mm. However, other embodiments may have varying lengths for each shank or blade section. For example, the blade sections 24 or 29 could have lengths varying form 4 mm to 21 mm. The width of the blade section could also vary from 1 mm to 3 mm.

Similar to TMPE 1A and 1B, each of the blade section (24 or 29) could also vary in shape. For example, the blade could be half-moon shaped or spear-shaped.

TMPE 2A comprises "bends" such as the junction between the first 21 and second 22 shanks, or the junction between the second 22 and third 23 shanks. Likewise, TMPE 2B also comprises "bends" at the junction between the first 26, second 27, and third 28 shanks. These "bends" provide a space for surgeons to used a finger to apply a measured amount of pressure so that attached gingiva can be elevated. The "bends" on these shanks allow the operator to apply pressure with a finger of a second hand with a degree of force under a control not available through the application of digital pressure with only one hand on the handle with a right-angled design. Furthermore, the unique angulations of instruments 2A and 2B allow the operator to gain a better line of sight for the indirect visualization of the movement of the blade as it engages the overlying tissue. As discussed above, the angled design of instruments 2A and 2B allow the instruments to be used on posterior teeth without impinging against the patient's facial features.

As illustrated in FIGS. 5A, 5B, 6A, and 6C, instruments TMPE 3A and 3B have similar angled designs as the 2A and 2B instruments, respectively. Further, 3A and 3B are "mirror images" of the 2A and 2B instruments, respectively. TMPE 3A and 3B instruments have similar uses and advantages as the 2A and 2B instruments, but are used in opposite quadrants of the mouth. For example, TMPE 2A can be used to reflect the flap distally in the upper right and lower left quadrants of the mouthy; TMPE 3A can be used to reflect the flap distally in the upper left and lower right quadrants. Likewise, TMPE 2B can be used to reflect the flap mesially in the upper right and lower left quadrants; TMPE 3B can be used to reflect the flap mesially in the upper left and lower right quadrants. Since the uses of TMPE instruments 3A and 3B are similar to those of 2A and 2B discussed above, detailed explanations of the uses of instruments 3A and 3B are omitted here.

As illustrated in FIGS. 5A, 5B, 6A, and 6C, TMPE instrument 3A comprises a shaft 30, a first shank 31 extending linearly from the shaft 30, a second shank 32 connected to the first shank 31 on one end and rotated from the first shank 31 at an angle c1 in the clockwise direction, a third shank 33 connected to a second end of the second shank 32 and rotated from the second shank at an angle c2 in the counter-clockwise direction, and a blade section 34 connected to the third shank 33 rotated at an angle c3 from the third shank 33 in the clockwise direction.

Also illustrated in FIGS. 5A, 5B, 6A, and 6B, TMPE instrument 3B comprises a shaft 35, a first shank 36 extending linearly from the shaft 35, a second shank 37 connected to the first shank 36 on one end and rotated from the first shank 36 at an angle c4 in the clockwise direction, a third shank 38 connected to a second end of the second shank 37 and rotated from the second shank at an angle c5 in the clockwise direction, and a blade section 39 connected to the third shank 38 rotated at an angle c6 from the third shank 38 in the counter-clockwise direction.

For TMPE instrument 3A and 3B, the second shanks (32 and 37) and third shanks (33 and 38) act as connector sections that connect the blade sections (34 and 39) to the handles (30 and 25) and first shanks (31 and 36).

For one preferred embodiment of TMPE instruments 3A and 3B, the angles c1-c6 correspond generally to the angles of b1-b6 for TMPE 2A and 2B. In one preferred embodiment, the angles for c1-c6 are approximately 60 degrees, 60 degrees, 90 degrees, 100 degrees, 110 degrees, and 90 degrees, respectively. For various other embodiments, the ranges of angles for c1-c6 are the same as the ranges discussed above for angles b1-b6 relating to TMPE 2A and 2B, and will not be repeated here.

For one embodiment of TMPE 3A as illustrated in FIGS. 5A, 5B, 6A, and 6B, the length of the second shank 32 is approximately 11 mm, the length of the third shank 33 is approximately 8 mm, and the length of the blade section 34 is approximately 13 mm. For the embodiment of TMPE 3B shown in FIGS. 5A, 5B, 6A, and 6B, the length of the second shank 37 is approximately 6 mm, the length of the third shank 38 is approximately 11 mm, and the length of the blade section 39 is approximately 13 mm. However, other embodiments have varying lengths for each shank or blade section. For example, the blade sections 34 or 39 could have lengths varying form 4 mm to 21 mm. The width of the blade section could also vary from 1 mm to 3 mm. Similar to TMPE 1A and 1B, each of the blade section (34 or 39) could also vary in shape. For example, the blade could be half-moon shaped or spear-shaped. The orientations of the width direction of the blade sections 34 and 39 with respect to the shafts 30 and 35 are similar to that of the instruments 2A and 2B, and the detailed explanations will not be repeated here.

The above-described instruments 1A, 1B, 2A, 2B, 3A, and 3B are designed to create the incision and release the flap necessary for the Chao TMPE surgical techniques described in the above sections (FIG. 15, S01-S03). Next, a group of instruments used to elevate the papillae (FIG. 15, S04) is described below while referring to FIGS. 7A, 7B, 8A, 8B, 9A, 9B, 10A, 10B, 11A, 11B, 12A, and 12B. The papillae is the gum tissue between two neighboring teeth. Instruments 4A, 4B, 5A, 5B, 6A, and 6B are collectively known as the Chao Papillae Elevators.

First, FIGS. 7A, 7B, 8A, and 8B illustrate instruments 4A and 4B, which are one set of embodiments of the Chao Papillae Elevators called the Chao TMPE Universal Papillae Elevators. Except for the blade sections 43 and 48, instruments 4A and 4B are similar in shape and design to the TMPE instrument 1A and 1B.

As illustrated in FIGS. 7A, 7B, 8A, and 8B, instrument 4A is an instrument with a handle 40, a first shank 41 linearly extending from the handle 40, a second shank 42 connected to the first shank 41 at one end and rotated at an angle d1 from the first shank 41 in the counter-clockwise direction, and a blade section 43 rotated at an angle d2 from the second shank 42 in the clockwise direction and connected to a second end of the second shank 42.

Also illustrated in FIGS. 7A, 7B, 8A, and 8B, instrument 4B is an instrument with a handle 45, a first shank 46 linearly extending from the handle 45, a second shank 47 connected to the first shank 46 at one end and rotated at an angle d3 from the first shank 45 in the clockwise direction, and a blade section 48 rotated at an angle d4 from the second shank 47 in the counter-clockwise direction and connected to a second end of the second shank 47.

In one preferred embodiment, the angles d1-d4 are all 90 degrees. Further, for instruments 4A and 4B, the blade sections 43 or 48 are orthogonal to the planes formed by the length directions of the first and second shanks 41 and 42, or 46 and 47, respectively. In various embodiments, the variations for the angles d1-d4, as well as the variations to the lengths of the first (41 or 46) and second (42 or 47) shanks are similar to that of instruments 1A and 1B, and the corresponding descriptions are therefore not be repeated here.

Figure 14B:
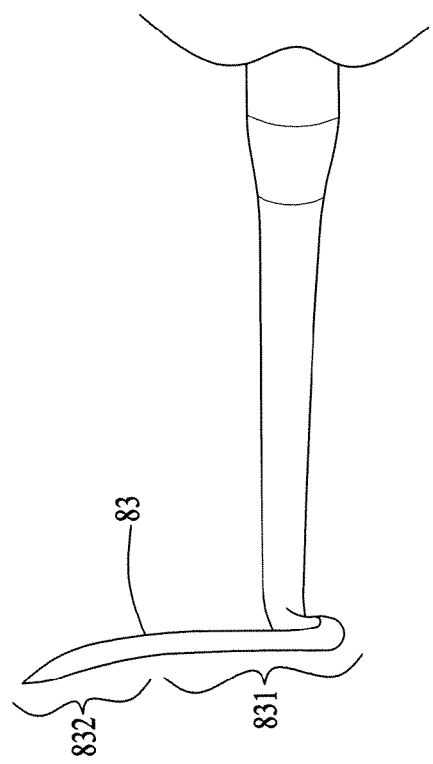
FIGS. 14A and 14B illustrate side views of the blade designs of instruments 1A and 4A, according to some varying embodiments.
Figure 14A:
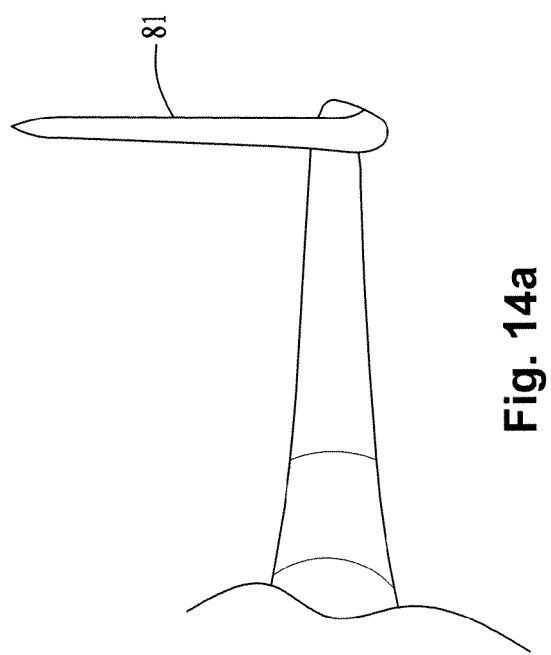

The differences between instrument 1A and 1B with 4A and 4B, respectively, are differences in the shape and dimension of the blade sections. FIGS. 14A and 14B illustrate a side-view comparison of between a blade section 81 for instruments 1A or 1B, and a blade section 83 for instruments 4A and 4B. For instrument 1A and 1B, the blade sections are relatively straight. On the other hand, for instruments 4A and 4B, the blade sections are shaped like a claw with a curved tip.

As illustrated in FIGS. 14A and 14B, the claw-like blade section for instruments 4A and 4B have a relatively straight section 831 and a curved section 832. In various embodiments, the curvature of the curved section 832 can vary from 10-30 degrees. Further, the curved section 832 is sharp and shaped like an arrow-head. In one preferred embodiment, the lengths of the blade sections 43 and 48 are each 13 mm. In various other embodiments, the lengths of the blade sections 43 and 48 could vary from 4 mm to 21 mm.

Figure 13C:
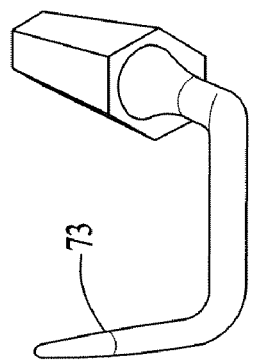
FIGS. 13A, 13B, and 13C illustrate top views of the blade designs of instruments 1A and 4A, according to some varying embodiments.
Figure 13B:
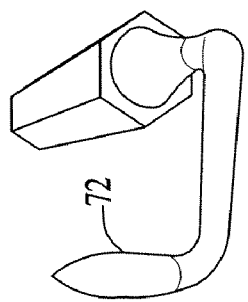
Figure 13A:
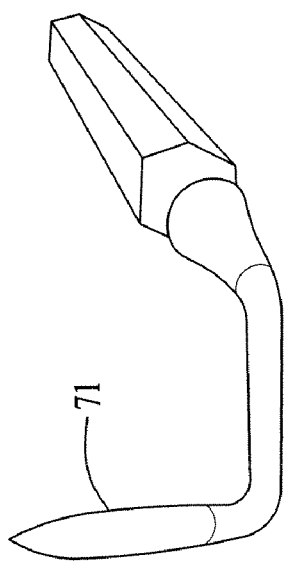

FIGS. 13A, 13B and 13C compare a top view of the blade section for instrument 1A and 4A. Blade section 71 is one embodiment of a longer spear-shaped blade section for instrument 1A. Blade section 72 is one embodiment of a shorter spear-shaped blade section for instrument 1A. Blade section 73 is one embodiment of a narrow claw-like blade section for instrument 4A. For the blade section of 1A, the width is typically 1-3 mm with sharp cutting edges along both side edges. For the blade section of 4A, the width is typically less than or equal to 2 mm, with a sharp top tip but no side cutting edges. Various designs for blade sections of instruments 1B and 4B are similar to those for instruments 1A and 4A, and are not illustrated.

The sharp and narrow blade sections 43 and 48 of instruments 4A and 4B, respectively, are designed to fit into the interproximal spaces (spaces between neighboring teeth) to release and elevate the papilla from its attachments to the root surfaces and the underlying bone. Instrument 4A can be used to elevate the papillae distal to the incision in the upper right and lower lower quadrants, as well as the papillae mesial to the incision in the lower right and upper left quadrants. Instrument 4B can be used to elevate the papillae mesial to the incision in the upper right and lower left quadrants of the mouth, as well as the papillae distal to the incision in the lower right and upper left quadrants of the mouth.

As illustrated in FIGS. 9a, 9b, 10a AND 10c, instruments 5A and 5B are papillae elevators with similar shapes and designs as instruments 2A and 2B, respectively. As shown in FIGS. 9-10, instrument 5A comprises a shaft 50, a first shank 51 extending linearly from the shaft 50, a second shank 52 connected to the first shank 51 on one end and rotated from the first shank 51 at an angle e1 in the counter-clockwise direction, a third shank 53 connected to a second end of the second shank 52 and rotated from the second shank 52 at an angle e2 in the clockwise direction, and a blade section 54 connected to the third shank 53 rotated at an angle e3 from the third shank 53 in the clockwise direction.

Also shown in FIGS. 9A, 9B, 10A, and 10C, instrument 5B comprises a shaft 55, a first shank 56 extending linearly from the shaft 55, a second shank 57 connected to the first shank 56 on one end and rotated from the first shank 56 at an angle e4 in the counter-clockwise direction, a third shank 58 connected to a second end of the second shank 57 and rotated from the second shank 57 at an angle e5 in the counter-clockwise direction, and a blade section 59 connected to the third shank 58 rotated at an angle e6 from the third shank 58 in the clockwise direction.

In one preferred embodiment, the angles e1-e6 are 60 degrees, 60 degrees, 90 degrees, 100 degrees, 110 degrees, and 90 degrees. In various other embodiments, the angles e1-e6 could vary within the same range as those for b1-b6, respectively. As with instruments 2A and 2B, for each of instruments 5A or 5B, the length direction of the blade section (54 or 59) is orthogonal to the plane formed by the first (51 or 56), second (42 or 57), and third (53 or 58) shanks. Since the lengths of the second (52 or 57) and third (53 or 58) shanks are also similar to that of the second (22 or 27) and third (23 or 28) shanks of instruments 2A and 2B, the discussion for the shank lengths are omitted here.

FIGS. 11A, 11B, 12A, and 12B illustrate papillae elevator instruments 6A and 6B, which are similar in design to instruments 3A and 3B. As illustrated in FIGS. 11A, 11B, 12A, and 12B, instrument 6A comprises a shaft 60, a first shank 61 extending linearly from the shaft 60, a second shank 62 connected to the first shank 61 on one end and rotated from the first shank 61 at an angle f1 in the clockwise direction, a third shank 63 connected to a second end of the second shank 62 and rotated from the second shank at an angle f2 in the counter-clockwise direction, and a blade section 64 connected to the third shank 63 rotated at an angle f3 from the third shank 63 in the clockwise direction.

Also illustrated in FIGS. 11A, 11B, 12A, and 12B, instrument 6B comprises a shaft 65, a first shank 66 extending linearly from the shaft 65, a second shank 67 connected to the first shank 66 on one end and rotated from the first shank 66 at an angle f4 in the clockwise direction, a third shank 68 connected to a second end of the second shank 67 and rotated from the second shank at an angle f5 in the clockwise direction, and a blade section 69 connected to the third shank 68 rotated at an angle c6 from the third shank 68 in the counter-clockwise direction.

In one preferred embodiment, the angles f1-f6 are 60 degrees, 60 degrees, 90 degrees, 100 degrees, 110 degrees, and 90 degrees. In various other embodiments, the angles f1-f6 could vary within the same range as those for c1-c6, respectively. As with instruments 3A and 3B, for each of instruments 6A or 6B, the length direction of the blade section (64 or 69) is orthogonal to the plane formed by the first (61 or 66), second (62 or 67), and third (63 or 68) shanks. Since the lengths of the second (62 or 67) and third (63 or 68) shanks are also similar to that of the second (32 or 37) and third (33 or 38) shanks of instruments 3A and 3B, the discussion for the shank lengths are omitted here.

For each of instruments 5A, 5B, 6A, and 6B, the blade sections (54, 59, 64, and 69, respectively) are narrow and claw-like as illustrated by the blade section 83 in FIG. 14B, which further comprises a relatively straight section 831 and a curved section 832. In various embodiments, the curvature of the curved section can vary from 10-30 degrees. Further, the curved section is sharp and shaped like an arrow-head. In one preferred embodiment, the lengths of the blade sections (54, 59, 64, and 69) are each 13 mm. In various other embodiments, the lengths of the blade sections 43 and 48 could vary from 4 mm to 21 mm. Since the design of the blade sections (54, 59, 64, and 69) for instruments 5A, 5B, 6A, and 6B are similar to that of the blade section for instrument 4A, the detailed descriptions are omitted here.

The sharp and narrow blade sections 54, 59, 64, and 69 of instruments 5A, 5B, 6A, and 6B, respectively, are designed to fit into the interproximal spaces (spaces between neighboring teeth) to release and elevate the papilla from its attachments to the root surfaces and the underlying bone. Like instruments 2A, 2B, 3A, and 3B, instruments 5A, 5B, 6A, and 6B are angled such that they can reach posterial surgical sites, e.g., buccal to second bicuspids or first molars, without impinging the patient's facial features. In addition, the "bends" on instruments 5A, 5B, 6A, and 6B provide access to the operator to apply pressure, just as the "bends" on instruments 2A and 2B discussed in detail above.

Instrument 5A can be used in the upper right and lower left quadrants of the mouth to elevate papillae distal to the incision. Instruments 5B can be used in the upper right and lower left quadrants to elevate papillae mesial to the incision. Instrument 6A can be used in the upper left and lower right quadrants of the mouth to elevate papillae distal to the incision. Instruments 6B can be used in the upper left and lower right quadrants of the mouth to elevate papillae mesial to the incision.

For preferred embodiments of each of instruments 1A, 1B, 2A, 2B, 3A, 3B, 4A, 4B, 5A, 5B, 6A, and 6B, the blade section comprises a cutting surface such that the plane of the cutting surface is substantially parallel to the length direction of the shank immediately connecting to the blade section. For example, as illustrated in FIGS. 4A and 4B, for instrument 2A, the blade section 24 has a cutting surface lying on a plane substantially parallel to the length direction of the third shank 23. As illustrated in FIG. 16(a)-(b), during horizontal extension of the flap, the blade sections must extend horizontally in the same direction as the shank immediately connecting to the blade section. In some of these preferred embodiments, the plane of the cutting surface of the blade section is exactly parallel to the length direction of the shank immediately connecting to the blade section. In some of these preferred embodiments, the plane of the cutting surface of the blade section is within +/−10 degrees of being parallel to the length direction of the shank immediately connecting to the blade section. This feature enables the horizontal extension of the flap without increasing the incision size, and is not found on any conventional instruments on the market today.

In some preferred embodiments, for each of instruments 1A, 1B, 2A, 2B, 3A, 3B, 4A, 4B, 5A, 5B, 6A, and 6B, the handle, first shank and connector section are integrally formed of the same material. In other embodiments, the handle, first shank, connector section, and blade section are all integrally formed of the same material. As described above, the connector section may comprise the second shank (instruments 1A, 1B, 4A, and 4B) or the second and third shanks (instruments 2A, 2B, 3A, 3B, 5A, 5B, 6A and 6B).

In some preferred embodiments, each of instruments 1A, 1B, 2A, 2B, 3A, 3B, 4A, 4B, 5A, 5B, 6A, and 6B is composed of surgical-grade stainless steel, titanium, or titanium nitride.

One method of manufacturing each of instruments 1A, 1B, 2A, 2B, 3A, 3B, 4A, 4B, 5A, 5B, 6A, and 6B comprises the steps of forming blanks using 440A stainless steel, coining and sanding the blanks into shape, shaping the blanks into the dimensions and geometries required by design, bending the tip to the specific angle of the instrument, heat treat the tip to the proper hardness of RC 50-52, assemble the tips with the handle, polishing the tip to remove the heat treat finish, sharpen the tips to form the cutting surface of the blade section, cleaning and buffing the instrument, and electro-etching the part number and description.

The Chao TMPE approach to gingival correction (gingival augmentation) described above is also applicable to correct gingival recession near the root of an implant. A dental implant is an artificial tooth root that a periodontist places into your jaw to hold a replacement tooth or bridge. First, the implant, which looks like a screw or cylinder, is placed into a patient's jaw in the place of a missing tooth. Over a period of time (often two to six months), the implant and the bone are allowed to bond together to form an anchor for the artificial tooth. Next, a small metal post, called an abutment, is put into the implant. Lastly, an artificial tooth (or called crown) is secured onto the abutment. Often, the gum line near an implant can recede, exposing the abutment. This is cosmetically unappealing for the patient, and could create other complications as well.

The Chao TMPE approach described above, as well as the instruments (1A, 1B, 2A, 2B, 3A, 3B, 4A, 4B, 5A, 5B, 6A, and 6B) can be used to repair the receding gum line near an implant in substantially the same steps as described above for a natural tooth. However, sometimes instruments used in the procedure may cause damages to the implant. Further, because the implants are typically composed of titanium, using an instrument composed of a dissimilar metal material could cause contamination. In some preferred embodiments where the instruments are intended to be used on patients with implants, each of the blade sections for instruments 1A, 1B, 2A, 2B, 3A, 3B, 4A, 4B, 5A, 5B, 6A, and 6B is coated with a protectant layer, such as Teflon or other suitable material, to avoid damage to the implant surfaces. In one embodiment, the tip of the blade sections for each of instruments 1A, 1B, 2A, 2B, 3A, 3B, 4A, 4B, 5A, 5B, 6A, and 6B is composed of a titanium-nitride (TiN) alloy material. In another embodiment, the tip of the blade sections for each of instruments 1A, 1B, 2A, 2B, 3A, 3B, 4A, 4B, 5A, 5B, 6A, and 6B is composed of a synthetic material. In yet another embodiment, the tip of the blade sections for each of instruments 1A, 1B, 2A, 2B, 3A, 3B, 4A, 4B, 5A, 5B, 6A, and 6B is coated with a layer of titanium-nitride (TiN) material.

The foregoing descriptions of embodiments of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For example, the above embodiments describe the lengths of various elements of the instruments and the angle between adjoining elements of the instruments. These measurements are intended to illustrate the best modes known of practicing the invention, and do not preclude various modifications and variations within the scope of this invention. Another example is that the blade sections of the embodiments of instruments described above are shown to be substantially straight or slightly curved. However, the blade sections may be curved anywhere from 0 degrees to 75 degrees and still be capable of performing the desired functions. Further, the blade shape is not limited to those described above, as various other blade shape designs could also perform the same functions.

In summary, the embodiments described hereinabove are intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An instrument for performing periodontal surgery, comprising:
   a handle having a linear length portion that has a single linear axial dimension;
   a connector section comprising a first end and a second end, the first end connecting to the handle; and,
   a blade section consisting of no more than one linear lengthwise dimension extending from the second end of the connector section;
   wherein,
   the connector section consisting of no more than one linear lengthwise dimension extending from the first end to the second end of the connector section;
   the no more than one linear lengthwise dimension of the connector section intersecting with the single linear axial dimension of the handle;
   the second end of the connector section is connected to the blade section such that the no more than one linear lengthwise dimension of the connector section intersects with the no more than one linear lengthwise dimension of the blade section;
   the single linear axial dimension of the handle and the no more than one linear lengthwise dimension of the connector section form a first angle;
   the no more than one linear lengthwise dimension of the connector section and the no more than one linear lengthwise dimension of the blade section form a second angle;
   the blade section comprises a cutting surface, said connector section and the handle lay in and extend along a first plane at the first angle in the first plane relative to each other, and the connector section and the cutting surface lay in and extend along a second plane at the second angle in the second plane relative to each other; and
   the first plane and the second plane are intersecting;
   a first cutting edge having a linear dimension that is located at one end of the cutting surface and a second cutting edge having a linear dimension that is facing away from the first cutting edge located at an opposing end of the cutting surface.

2. The instrument of claim 1, wherein the linear dimension of the first cutting edge is within a range of 4 to 21 mm long; and wherein the linear dimension of the second cutting edge is within a range of 4 to 21 mm.

3. The instrument of claim 1, wherein each of the first angle and the second angle is between 80-100 degrees, and the connector section comprises a straight shank.

4. The instrument of claim 3, wherein the first angle is approximately 90 degrees in the counter-clockwise direction, and the second angle is approximately 90 degrees in the clockwise direction.

5. The instrument of claim 3, wherein the first angle is approximately 90 degrees in the clockwise direction, and the second angle is approximately 90 degrees in the counter-clockwise direction.

6. The instrument of claim 1, wherein the blade section is one of either a half-moon shape or a spear shape.

7. The instrument of claim 1, further comprising a first shank extending linearly from the handle, wherein the connector section connects to the handle through the first shank.

8. The instrument of claim 1, wherein the blade section is 1-3 mm wide and comprises a sharp point with cutting edges on two sides.

9. The instrument of claim 1, wherein the blade section is thin and needle-like.

10. The instrument of claim 1, wherein the blade section is composed of one of surgical-grade stainless steel, titanium, and titanium-nitride (TiN).

11. The instrument of claim 10, wherein the blade section further comprises a protecting coating of Titanium Nitrite (TiN).

12. The instrument of claim 3, wherein the connector section is approximately 11 mm long, and the blade section is approximately 13 mm long.

13. The instrument of claim 1, wherein the handle comprises a first end and a second end, the second end of the handle connecting to the first end of the connector section and the handle consisting of no more than one linear lengthwise dimension extending from the first end of the handle to the second end of the handle.

14. An instrument for performing periodontal surgery, comprising:
    a handle having a linear length portion that has a single linear axial dimension;
    a connector section comprising a first end and a second end, the first end connecting to the handle; and,
    a blade section consisting of no more than one linear lengthwise dimension extending from the second end of the connector section;
    wherein,
    the connector consisting of no more than one linear lengthwise dimension extending from the first end to the second end of the connector section;
    the no more than one linear lengthwise dimension of the connector section intersecting with the single linear axial dimension of the handle;
    the second end of the connector section is connected to the blade section such that the no more than one linear lengthwise dimension of the connector section intersects with the no more than one linear lengthwise dimension of the blade section;

the single linear axial dimension of the handle and the no more than one linear lengthwise dimension of the connector section form a first angle;

the no more than one linear lengthwise dimension of the connector section and the no more than one linear lengthwise dimension of the blade section form a second angle;

the blade section comprises a cutting surface, said connector section and the handle lay in and extend along a first plane at the first angle in the first plane relative to each other, and the connector and the cutting surface lay in and extend along a second plane at the second angle in the second plane relative to each other; and the first plane and the second plane are intersecting;

a first cutting edge having a linear dimension that is located at one end of the cutting surface and a second cutting edge having a linear dimension that is located at an opposing end of the cutting surface;

wherein the connector section is within a range of 4-18 mm long, and the blade section is within a range of 4-21 mm long.

15. The instrument of claim 1, wherein the handle and connector section are integrally formed of a same material.

16. The instrument of claim 1, further comprising an angle between intersection the first plane and the second plane being about 80 degrees to 100 degrees.

17. The instrument of claim 14, wherein the handle comprises a first end and a second end, the second end of the handle connecting to the first end of the connector section and the handle consisting of no more than one linear lengthwise dimension extending from the first end of the handle to the second end of the handle.

18. An instrument for performing periodontal surgery, comprising:

a handle;

a connector connecting the handle to a cutting surface, the cutting surface consisting of no more than one linear lengthwise dimension extending from the connector;

the handle having a linear length portion having a single linear axial dimension and the connector consisting of no more than one linear lengthwise dimension, a linear length portion of the connector extending linearly from a first end to a second end of the connector, the first end of the connector connected to the handle and the no more than one linear lengthwise dimension of the connector intersects with the single linear axial dimension of the handle; and the second end of the connector is connected to the cutting surface such that the no more than one linear lengthwise dimension of the connector intersects the no more than one linear lengthwise dimension of the cutting surface;

wherein the single linear axial dimension of the handle and the no more than one linear lengthwise dimension of the connector are at a non-zero angle relative to each other and the single linear axial dimension of the handle and the no more than one linear lengthwise dimension of the connector each extend along a respective direction that lays in and extends along a first plane;

wherein the no more than one linear lengthwise dimension of the connector and the no more than one linear lengthwise dimension of the cutting surface are at a non-zero angle relative to each other;

the cutting surface having a first linear cutting edge and a second linear cutting edge that are generally perpendicular to both the single linear axial dimensions of the handle and no more than one linear lengthwise connector, where the first and second linear cutting edges are located on opposing sides of the cutting surface.

19. An instrument for periodontal surgery, the instrument comprising:

a handle having a single linear length section having a single linear axial dimension that extends along a first plane;

a connector consisting of no more than one linear lengthwise dimension, the connector having a single linear length section that extends along a second plane, the first plane and the second plane intersect;

wherein the single linear length section of the connector extending linearly from a first end to a second end of the connector;

wherein the no more than one linear lengthwise dimension of the connector intersects with the single linear axial dimension of the handle;

a cutting surface consisting of no more than one linear lengthwise dimension extending from the second end of the connector;

wherein the second end of the connector is connected to the cutting surface such that the single axial dimension of the connector intersects with the no more than one linear lengthwise dimension of the cutting surface;

wherein the second end of the connector connects to a first cutting edge having a linear length portion extending along a single linear axial dimension and a second cutting edge having a linear length portion extending along a single linear axial dimension, the cutting edges extending along a third plane;

wherein the no more than one linear lengthwise dimension of the connector intersects with the single linear axial dimension of the first cutting edge; and wherein the single linear axial dimension of the handle and the no more than one linear lengthwise dimension of the connector intersect with the single linear axial dimensions of the first and second cutting edges.

20. The instrument of claim 19, wherein the first plane intersects with the second plane at an angle greater than 60 degrees.

21. The instrument of claim 19, wherein the second plane intersects with the third plane at an angle greater than 60 degrees.

22. The instrument of claim 19, wherein the first plane is orthogonal to the second plane.

23. The instrument of claim 19, wherein the second plane is orthogonal to the third plane.

24. The instrument of claim 1, wherein the length dimension of the cutting edges is configured to be parallel to the length dimension of an anterior tooth surface while the handle is substantially perpendicular to the anterior tooth surface.

25. The instrument of claim 1, wherein the first and second cutting edges taper toward each other to form a sharp point at an end of the cutting surface.

26. The instrument of claim 1, wherein the connector section has a straight, linear portion extending within a range of 4-18 mm long.

27. The instrument of claim 1, wherein the length dimension of the cutting edges has a straight, linear portion extending within a range of 4-21 mm long.

28. The instrument of claim 1, wherein the connector section is within a range of 4-18 mm long, and the blade section is within a range of 4-21 mm long.

29. The instrument of claim 1, wherein the cutting surface has a central axis that extends along a length dimension of the cutting surface and the first edge is located on one side of the central axis and the second edge is located on the other side of the central axis.

30. The instrument of claim 1, wherein the handle has a central axis that extends along a length dimension of the handle; wherein the blade section is configured to be laterally offset from the central axis of the handle.

31. The instrument of claim 14, wherein the blade section has a straight, linear portion extending within a range of 4-21 mm long.

32. The instrument of claim 14, wherein the blade section has a straight, linear portion extending within a range of 4-18 mm long.

33. The instrument of claim 18, wherein the handle comprises a first end and a second end, the second end of the handle connecting to the first end of the connector and the handle consisting of no more than one linear lengthwise dimension extending from the first end of the handle to the second end of the handle.

34. The instrument of claim 19, wherein the handle comprises a first end and a second end, the second end of the handle connecting to the first end of the connector and the handle consisting of no more than one linear lengthwise dimension extending from the first end of the handle to the second end of the handle.

* * * * *